(12) United States Patent
Pinney et al.

(10) Patent No.: US 7,893,261 B2
(45) Date of Patent: Feb. 22, 2011

(54) SEROTONIN REUPTAKE INHIBITORS

(75) Inventors: Kevin G. Pinney, Woodway, TX (US); Maria Graciela Miranda, Waco, TX (US); James Michael Dorsey, Durham, NC (US)

(73) Assignee: Baylor University, Waco, TX (US)

( * ) Notice: Subject to any disclaimer, the term of this patent is extended or adjusted under 35 U.S.C. 154(b) by 423 days.

(21) Appl. No.: 10/594,105

(22) PCT Filed: Mar. 28, 2005

(86) PCT No.: PCT/US2005/010356
§ 371 (c)(1), (2), (4) Date: Sep. 21, 2007

(87) PCT Pub. No.: WO2005/094896
PCT Pub. Date: Oct. 13, 2005

(65) Prior Publication Data
US 2008/0132514 A1    Jun. 5, 2008

Related U.S. Application Data

(60) Provisional application No. 60/557,069, filed on Mar. 26, 2004.

(51) Int. Cl.
C07D 239/02    (2006.01)
C07D 295/00    (2006.01)
C07D 211/30    (2006.01)
C07D 211/32    (2006.01)

(52) U.S. Cl. .................. 544/297; 546/225; 544/395

(58) Field of Classification Search ............ 514/255.03, 514/275, 330; 544/297, 395; 546/225
See application file for complete search history.

(56) References Cited

U.S. PATENT DOCUMENTS 6,221,613 B1 * 4/2001 Salon et al. ................. 435/7.1

FOREIGN PATENT DOCUMENTS

| EP | 0 576 766 | * | 6/1992 |
| EP | 0 576 766 | A1 | 1/1994 |
| EP | 0 966 966 | A2 | 12/1999 |
| WO | WO 00/72832 | A2 | 12/2000 |
| WO | WO 02/39989 | A1 | 5/2002 |
| WO | WO 02/40024 | A1 | 5/2002 |
| WO | WO 02/060392 | A2 | 8/2002 |
| WO | WO 2004/082686 | A2 | 9/2004 |
| WO | WO 2005/058835 | A2 | 6/2005 |

OTHER PUBLICATIONS

Oficialdegui, et al., Design, Synthesis and Biological Evaluation of New 3-[(4-aryl)piperazin-1-yl]-1-arylpropane Derivatives as Potential Antidepressants with a Dual Mode of Action; Serotonin Reuptake Inhibition and 5-HT1A Receptor Antagonism, Farmaco 55(5), 345-353 (2000).*

Martinez-Esparza, et al., New 1-aryl-3-(4-arylpiperazin-1-yl)propane derivatives, with dual action at 5-HT1A serotonin receptors and serotonin transporter, as a new class of antidepressants, Journal of Medicinal Chemistry 44(3), 418-428, (2001).*

Dorsey, et al., Synthesis and Biological Evaluation of 2-(4-fluorophenoxy)-2-phenyl-ethyl Piperazines as Serotonin-selective Reuptake Inhibitors with a Potentially Improved Adverse Reaction Profile, Bioorganic & Med. Chem., 12, 1483-91 (2004).*

Pierre B, De Montigny C, Chaput Y. A Role for the Serotonin System in the Mechanism of Action of Antidepressant Treatments: Preclinical Evidence, J Clin Psychiatry 51:4 (Supp), Apr. 1990: 14-21.

Gonzalez-Heydrich J, Peroutka S J. Serotonin Receptor and Reuptake Sites: Pharmacologic Significance, J Clin Psychology 51:4 (Supp), Apr. 1990: 5-13.

Hytell J. Citalpram-Pharmacological Profile of a Specific Serotonin Uptake Inhibitor with Antidepressant Activity, Prog. Neuro-Psychopharmacal & Biol. Psychiat. vol. 6. 1982: 277-295.

Modell J G, Katholi C R, Modell, J D, DePalma R L. Pharmacoepidemiology and Drug Utilization-Comprative Sexual Side Effects of Bupropion, Fluoxetine, Paroxetine, and Sertraline, Clinical Pharmacology & Therapeutics vol. 61 No. 4, 1997: 476-487.

Munson P J, Rodbard D. Ligand: A Verstatile Computerized Approach for Characterization of Ligand-Binding Systems, Analytical Biochemistry 107, 1980: 220-239.

Lemberger L, Fuller R W, Zerbe R L. Use of Serotonin Uptake Inhibitors as Antidepressants, Clinical Neuropharmacology. vol. 8 No. 4, 1985: 299-317.

Orjales A, Mosquera R, Toledo A, Pumar M C, Garcia N, Cortizo L. Synthesis and Binding Studies of New [(Aryl)(aryloxy)methyl] piperidine Derivatives and Related Compounds as Potential Antidepressant Drugs with High Affinity for Serotonin (5-HT) and Norepinephrine (NE) Transporters.Journal of Medicinal Chemistry vol. 46 No. 25. 2003: 1512-1532.

Dorsey J M, Miranda M G, Cozzi N V, Pinney K G. Synthesis and biological evaluation of 2-(4-flourophenoxy)-2-phenyl-ethyl piperazines as serotonun-selective reuptake inhibitors with a potentially improved adverse reaction profile, Bioorganic & Medicinal Chemistry vol. 12, 2004: 1483-1491.

Cozzi N V, Foley K F. Rapid and Efficient Method for Suspending Cells for Neurotransmiter Uptake Assays, BioTechniques 32, Mar. 2002: 486-492.

(Continued)

Primary Examiner—James O Wilson
Assistant Examiner—Erich A Leeser
(74) Attorney, Agent, or Firm—Jackson Walker L.L.P.

(57) ABSTRACT

A serotonin reuptake inhibitor which can be used in the treatment of depression and which has a decreased occurrence of unwanted side effects. The serotonin reuptake inhibitors are bi-functional organic molecules which combine serotonin transporter reuptake inhibition with serotonin (5-HT, such as 5-HT2A) receptor antagonism in one molecular entity. The serotonin-selective reuptake inhibitor (SSRI) homologue portion of the molecule shows an affinity to the serotonin reuptake transporter (SERT) and has antidepressant properties. The piperazine or piperidine portion of the molecule demonstrates an affinity to 5-HT receptors and restores the undesired side effects of SSRIs.

3 Claims, 11 Drawing Sheets

OTHER PUBLICATIONS

Dorsey JM, Miranda MG, Cozzi NV, Pinney KG. Synthesis and biological evaluation of 2-(4-fluorophenoxy)-2-phenyl-ethyl piperazines as serotonin-selective reuptake inhibitors with a potentially improved adverse reaction profile. Bioorg Med Chem. Mar. 15, 2004;12(6):1483-91.

Martinez-Esparza J, Oficialdegui AM, Perez-Silanes S, Heras B, Orus L, Palop JA, Lasheras B, Roca J, Mourelle M, Bosch A, Del Castillo JC, Tordera R, Del Rio J, Monge A. New 1-aryl-3-(4-arylpiperazin-1-yl)propane derivatives, with dual action at 5-HT1A serotonin receptors and serotonin transporter, as a new class of antidepressants. J Med Chem. Feb. 1, 2001;44(3):418-28.

Orjales A, Mosquera R, Toledo A, Pumar MC, Garcia N, Cortizo L, Labeaga L, Innerarity A. Syntheses and binding studies of new [(aryl)(aryloxy)methyl]piperidine derivatives and related compounds as potential antidepressant drugs with high affinity for serotonin (5-HT) and norepinephrine (NE) transporters. J Med Chem. Dec. 4, 2003;46(25):5512-32.

PCT Notification of Transmittal of the International Search Report and the Written Opinion of the International Searching Authority, or the Declaration dated Feb. 5, 2007.

* cited by examiner

| Homologues Type I | Homologues Type II |
|---|---|
|  |  |
| Aminoethane Derivatives<br>X = F or CF$_3$<br>A = N or C (piperazine or piperidine)<br>Ar = variety of aryl groups | Aminopropane Derivatives<br>X = F or CF$_3$<br>A = N or C (piperazine or piperidine)<br>Ar = variety of aryl groups | amantadine methylphenidate mianserin cyproheptadine yohimbine sildenafil citrate buspirone trazodone nefazodone X = F or CF$_3$
n = 0 or 1 (ethyl or propyl chain)
A = N or C (piperazine or piperidine)
Ar = variety of aryl derivatives

Scheme 1. Synthesis of Homologues Type II – Compounds 1 and 2.

*Reagents and conditions*: (i) Paraformaldehyde, cat. HCl, reflux 6h, 62%; (ii) NaBH$_4$ at 0°C, 8h at rt, 44-66%; (iv) THF, 4-fluorophenol or 4-trifluoromethylphenol, PPh$_3$, DIAD dropwise at 0°C, 48h at rt, 54-72%; (v) 2M HCl in anhydrous ether, 41-46%.

Scheme 2. Synthesis of Homologues Type I – Compounds 3 to 9.

*Reagents and conditions*: (i) K$_2$CO$_3$, Acetonitrile, reflux 16h, 53-59%; (ii) NaBH$_4$ at 0°C, 8h at rt, 91-95%; (iii) THF, 4-fluorophenol or 4-trifluoromethylphenol, PPh$_3$, DIAD dropwise at 0°C, 48h at rt, 40%; (iv) 2 M HCl in anhydrous ether, 75-81%.

Scheme 3. Synthesis of Homologues Type I – Compounds 10 to 12.

Where HNR₁R₂ =

*Reagents and Conditions*: i) t-boc anhydride, DMF, 15 min at 50°C, 8h at rt, 78%; ii) DMF, 4-fluorophenol, PPh3, DEAD dropwise at 0°C, 8h at rt, 43%; iii) 4N HCl in Dioxane, 1.5h at rt, 64%; iv) DMF, TiBr4, t-butyl nitrite, 1 h at rt, 33%; v) K₂CO₃, DMF, reflux 16-18h, 18-39%; vi) 2M HCL in anhydrous ether, 9-68%.

Scheme 4. Synthesis of Homologues Type I – Compounds 13 to 16.

*Reagents and conditions*: (i) $K_2CO_3$, Dichloromethane, reflux 16h, 53-59%; (ii) THF, 4-fluorophenol or 4-trifluoromethylphenol, $PPh_3$, DIAD dropwise at 0°C, 48h at rt, 40%; (iii) 2 M HCl in anhydrous ether, 75-81%.

SEROTONIN REUPTAKE INHIBITORS

BACKGROUND

This application claims priority to U.S. Provisional Patent Application, Ser. No. 60/557,069, entitled "NOVEL SEROTONIN REUPTAKE INHIBITORS" filed on Mar. 26, 2004, having Maria G. Miranda, Kevin G. Pinney, and James N. Dorsey, listed as the inventors, the entire content of which is hereby incorporated by reference.

This invention pertains to novel serotonin reuptake inhibitors which comprise a structural homologue of a serotonin reuptake inhibitor, known to treat depression, and a piperazine moiety, known to treat sexual dysfunction induced by serotonin-selective reuptake inhibitors (SSRIs).

Depression is a common, life-disrupting, potentially lethal illness that can affect both sexes and all ages. Untreated major depression remains a serious public health problem ands its incidences are staggering. Its peak onset is in the early adult years. Suicide occurs in as many as 15% of patients with depression, especially those with recurrent episodes and hospitalizations. Therefore it becomes evident that treatment of depression is a matter of prime importance. Depression has no single cause; often, it results from a combination of factors. Whatever its cause, depression is not just a state of mind. It is related to physical changes in the brain, and connected to an imbalance of a type of chemical that carries signals in the brain and nerves. These chemicals are called neurotransmitters. Among the most important neurotransmitters related with depression are serotonin (5-HT), norepinephrine (NE), and dopamine (DA). Serotonin plays a very important role in the mood disorders, especially in anxiety and depression, aggression and impulsivity. Regulation of the mood disorders is possible either by agonistic or antagonistic action on a certain type of the serotonin receptors.

Serotonin-selective reuptake inhibitors (SSRIs), such as fluoxetine (PROZAC®), have traditionally been the mainstay of treatment for clinical depression—replacing the more toxic tricyclic antidepressants (TCAs). SSRIs have a more favorable adverse reaction profile in comparison to the TCAs and are much easier to tolerate. SSRIs exert their therapeutic effect by blocking the reuptake of serotonin into the presynaptic nerve terminal, thus increasing the synaptic concentration of serotonin. It is also believed that SSRIs increase the efficacy of the serotonin (5-HT) neurons by desensitizing 5-HT autoreceptors located on the presynaptic 5-HT nerve terminals. The ability of the 5-HT autoreceptors to inhibit the release of 5-HT decreases after long-term treatment with SSRIs, with the net effect being that a greater amount of 5-HT is released per impulse. The release of 5-HT from these Neurons, thus, becomes more efficient.

Unfortunately, SSRIs are not innocuous drugs. In spite of the progress in the treatment of depression with the advent of the SSRIs, some troublesome side effects still remain—most notably, sexual dysfunction. As prescribing of SSRIs increased, the side effect of sexual dysfunction emerged, and clinicians searched for methods to treat or reverse SSRI-induced sexual dysfunction. A number of pharmacological agents—notably, drugs in the piperazine class—have been used to reverse SSRI-induced sexual dysfunction.

It is widely believed that a number of monoamine neurotransmitters have a role in the etiology of depression and, consequently, its treatment. The most notable of these neurotransmitters include norepinephrine (NE) and serotonin (5-HT). It is well known that inhibiting the reuptake of NE or 5-HT (or both) has elicited a favorable response in patients being treated for depression. Without question, however, inhibition of 5-HT reuptake has been the most widely studied, and treatment of depression has focused on inhibiting the reuptake mechanism of the neurotransmitter. Indeed, it was this premise which led to the hypothesis that altering 5-HT function could lead to an effective mechanism in the treatment of depression.

Research in the treatment of depression remains focused on 5-HT because a good number of selective 5-HT reuptake blockers tested in clinical trials have been effective in treating major depression. The general mechanism of action is hypothesized as enhanced 5-HT neurotransmission due to the increased availability of 5-HT in the synapse of these neurons (Blier et al., 1990). SSRIs generally have a 50- to 100-fold or greater selectivity for the inhibition of serotonin uptake in vitro when compared to their ability to inhibit NE or DA uptake (Lemberger et al., 1985).

Sexual dysfunction is a common problem in affective disorders such as major depression. It is important to note, however, that the drugs used in the treatment of depression can cause sexual dysfunction as well. Antidepressants such as the TCAs, monoamine oxidase inhibitors, and the SSRIs have all been reported to cause sexual side effects. The inhibitory effects of the SSRIs on sexual function are well documented, and the frequency of occurrence varies widely. By switching to a less serotonergic drug, it is surmised that the non-selective effects of 5-HT can be reduced within the synapse of the 5-HT neuron. Although the connection between serotonergic activity and sexual function is not straightforward, it is believed that the increased central serotonergic activity of SSRIs (at the receptor subtypes $5-HT_{1A}$, $5-HT_{1B}$, $5-HT_{2C}$, $5-HT_{2A}$ and $5-HT_3$) plays a role in the emergence of sexual dysfunction (Modell et al., 1997). It follows, therefore, that reducing the activity of SSRIs at these receptors could allow the suppression or inhibition of the sexual response to be corrected. Strategies which have been tried in treating or reversing sexual dysfunction include: titration of an antidepressant dose, scheduling of a drug holiday during treatment, and administering a second drug (along with an SSRI, for example) to counteract the SSRI's sexual side effects.

The drugs which have been administered along with an SSRI include a broad range of medicinal agents. Drugs such as: amantadine (normally used in the treatment of Parkinsonism), cyproheptadine, buspirone, trazodone, nefazodone, methylphenidate, mianserin, yohimbine, and even sildenafil citrate have been used. Bupropion has also been of benefit. The success of each of these agents varies widely, but the best studied agents include bupropion and buspirone (Hyttel, 1982). Buspirone, which has a pyrimidinyl-piperazine group, is generally used in the treatment of generalized anxiety disorder and has been used with some success in treating patients with SSRI-induced sexual dysfunction (Gonzalez-Heydrich, 1990) It is interesting to note that other piperazine-containing groups (specifically, functionalized phenylpiperazines) have likewise been used with success in treating sexual dysfunction. These agents include: sildenafil citrate, trazodone, and nefazodone.

What is needed, therefore, is an SSRI with an adverse reaction profile that is devoid of sexual side effects.

SUMMARY

The present invention relates to novel serotonin reuptake inhibitors. The reuptake inhibitors comprise bi-functional organic molecules which combine serotonin transporter reuptake inhibition with serotonin (5-HT, such as $5HT_{2A}$) receptor antagonism in one molecular entity. In particular, the serotonin reuptake inhibitors comprise a structural homologue of an antidepressant serotonin-selective reuptake inhibitor (SSRI) coupled to the piperidine or piperazine moiety of a compound having 5-HT receptor antagonism. The serotonin reuptake inhibitors may have a free amine group, or they may exist as salts, such as hydrochloride salts.

The SSRI portion of the molecule is most closely similar in structure to that of fluoxetine (Prozac®), shown in FIG. 1. There are two preferred types of homologues of the SSRI portion, an aminoethane derivative (Type I) and an aminopropane derivative (Type II), as shown in FIG. 2. The 5-HT receptor antagonist portion of the molecule is most closely similar in structure to the piperazinyl-containing portion of any of the compounds used to treat the side effects or sexual dysfunction caused by SSRIs. Examples are shown in FIG. 3. Thus, the :5-HT receptor antagonist portion of the molecule comprises a piperazine or piperidine moiety coupled to a variety of groups, most of which are aryl groups. FIG. 4 shows a generalized representation of the bi-functional molecules, in which Part a is the SSRI homologue having the ability to inhibit the serotonin reuptake transporter (SERT) and Part b is the piperazine or piperidine moiety which demonstrates antagonism to the 5-HT receptors.

One aspect of the present invention is a serotonin reuptake inhibitor having the general formula:

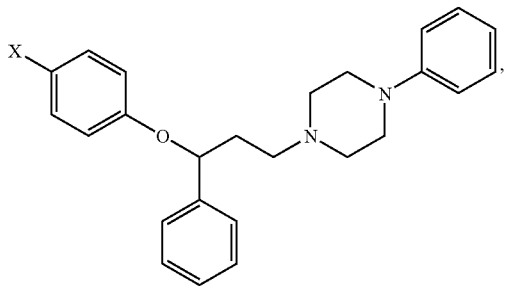

wherein X is F or CF$_3$; and salts thereof. This type of serotonin reuptake inhibitor is based on the Type II aminopropane derivative of the SSRI homologue.

Another aspect of the present invention is a serotonin reuptake inhibitor having the general formula:

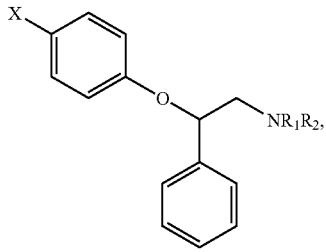

wherein X is F or CF$_3$;
wherein NR$_1$R$_2$ is:

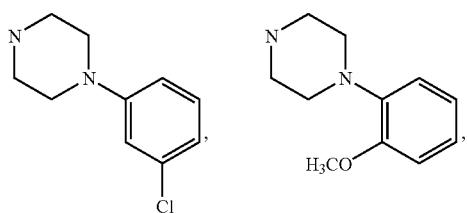

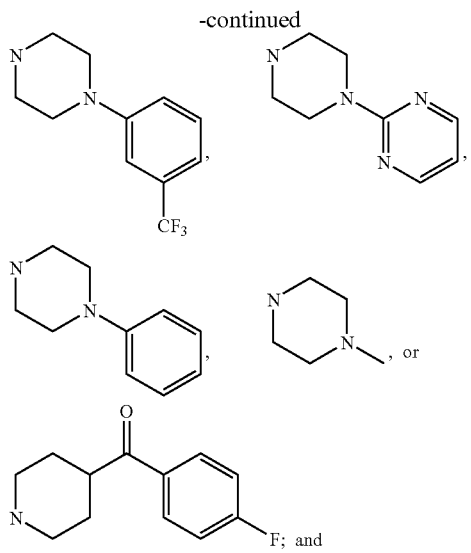

salts thereof. These types of serotonin reuptake inhibitors are based on the Type I aminoethane derivatives of the SSRI homologue.

DETAILED DESCRIPTION OF PREFERRED EMBODIMENTS

The present invention relates to serotonin reuptake inhibitors comprising an SSRI homologue coupled to a piperazine or piperidine moiety. The serotonin reuptake inhibitors are bi-functional organic molecules which combine 5-HT$_{2A}$ receptor antagonism and serotonin reuptake inhibition into one molecular entity. The SSRI homologue shows an affinity to the serotonin reuptake transporter (SERT) and has antidepressant properties. The piperazine or piperidine moiety demonstrates an affinity to 5-HT receptors and restores the undesired side effects of SSRIs.

One aspect of the present invention is a serotonin reuptake inhibitor having the general formula:

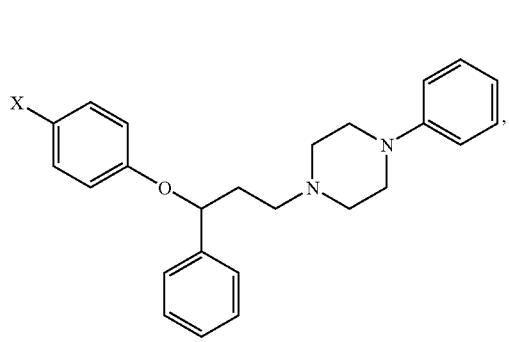

wherein X is F or $CF_3$; and salts thereof.

Another aspect of the present invention is a serotonin reuptake inhibitor having the general formula:

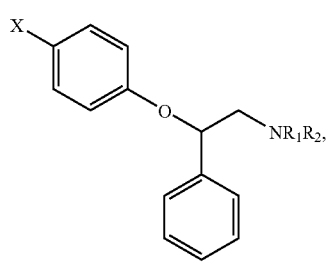

wherein X is F or $CF_3$;

wherein $NR_1R_2$ is:

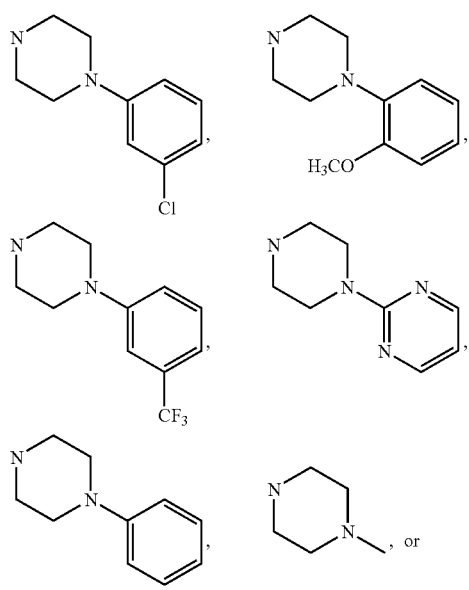

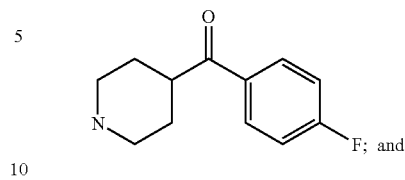

F; and salts thereof.

Preferred examples of the serotonin reuptake inhibitors were prepared according to the general synthetic schemes shown in Schemes 1-4 in FIGS. 5-8.

The serotonin reuptake inhibitors, and their salts, exhibit single-site binding at the site of the serotonin reuptake transporter (SERT) and inhibition of 5-HT receptor uptake.

EXAMPLE 1

General Methods

Chemicals used in synthesis were obtained from the Aldrich Chemical Company (St. Louis, Mo.), Fisher Scientific (Hampton, NH) and ACROS Chemicals (Belgium). Tetrahydrofuran (THF), dried with potassium and benzophenone, and methylene chloride, dried with calcium hydride, were freshly distilled immediately prior to use. Dimethylformamide (DMF) was purchased as an anhydrous commercial product in a SureSeal® container from the Aldrich Chemical Company. Silica gel plates for analytical thin layer chromatography (TLC) were obtained from EM Science (Gibbstown, N.J.). Column chromatography was performed using silica gel (300-400 mesh) obtained from Merck EM Science. $^1H$ and $^{13}C$ NMR were recorded in deuterated chloroform ($CDCl_3$) using an AMX 360 MHz (90 MHz for $^{13}C$) and/or DPX Avance 300 MHz (75 MHz for $^{13}C$) Bruker NMR spectrometers. Peaks are listed as broad (b), singlet (s), doublet (d), triplet (t), quartet (q), or multiplet (m), with the coupling constant (j) expressed in hertz (Hz). High resolution mass spectra were recorded using a VG/Fisons High Resolution GC/Mass Spectrometer using perfluorokerosene (PFK) as the calibration standard. All elemental analyses were conducted by Atlantic Microlab, Inc. in Norcross, Ga. Melting points were determined in open capillary tubes using a Thomas-Hoover electronically heated melting point apparatus and are uncorrected.

EXAMPLE 2

Synthesis of Compounds 1 and 2

Figure 1:
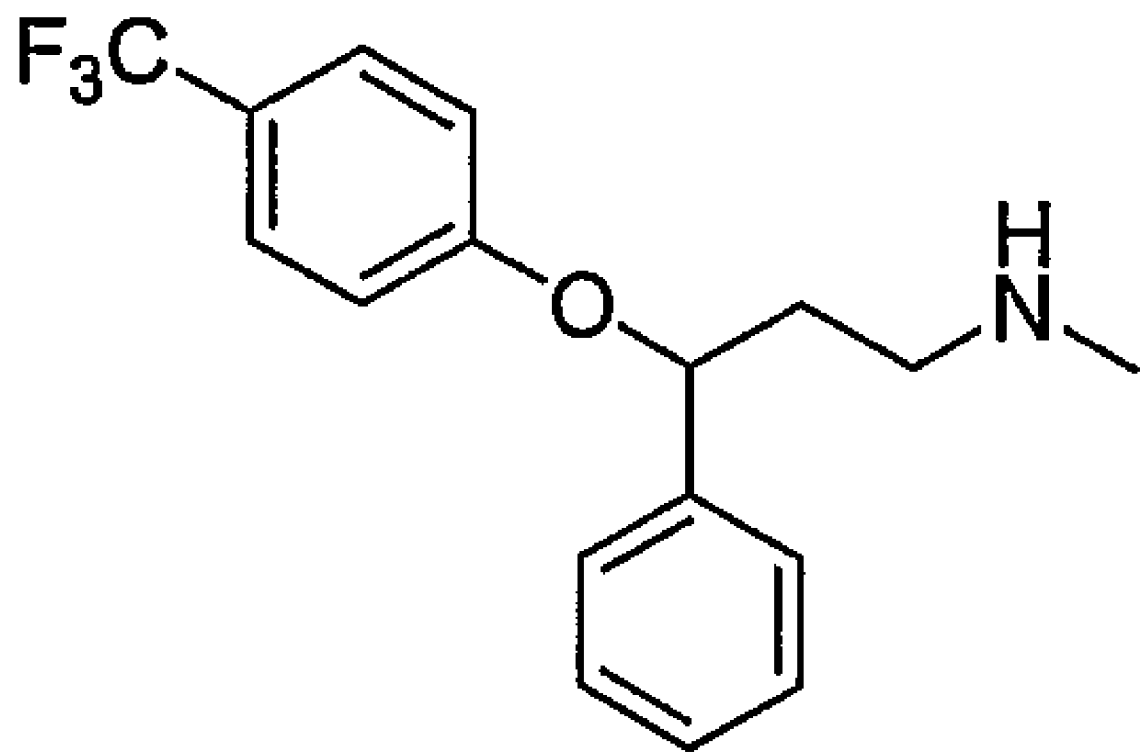
FIG. 1 shows the structure of fluoxetine (Prozac®).
Figure 2:
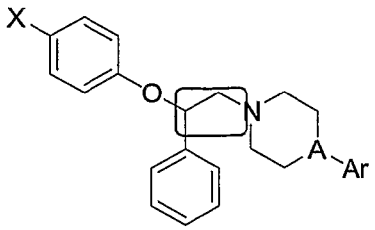
FIG. 2 shows two types of SSRI homologues, an aminoethane derivative (Type I) and an aminopropane derivative (Type II).
Figure 2:
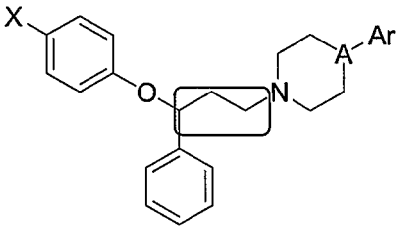
Figure 3:
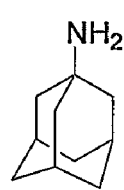
FIG. 3 shows examples of drugs traditionally administered with an SSRI to reverse or treat sexual dysfunction.
Figure 3:
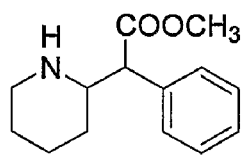
Figure 3:
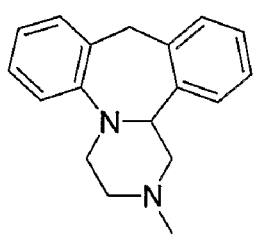
Figure 3:
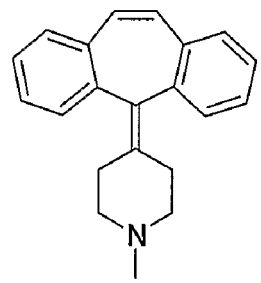
Figure 3:
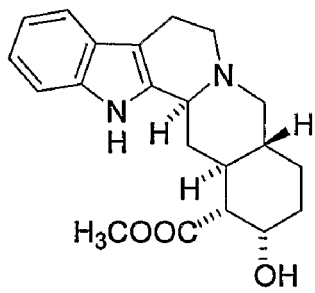
Figure 3:
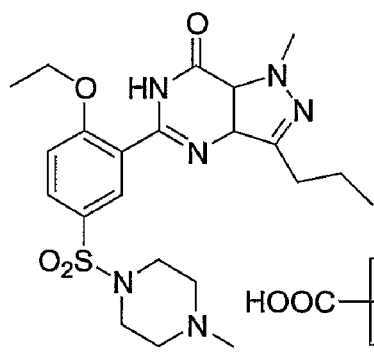
Figure 3:
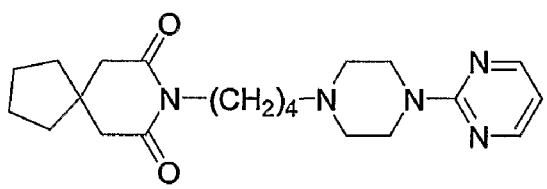
Figure 3:
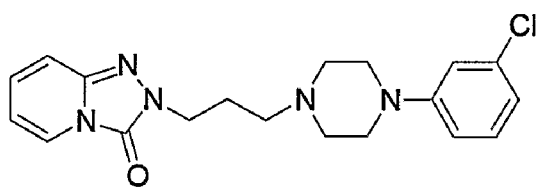
Figure 3:
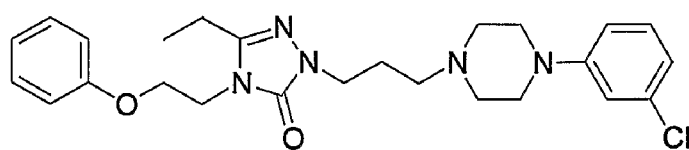
Figure 4:
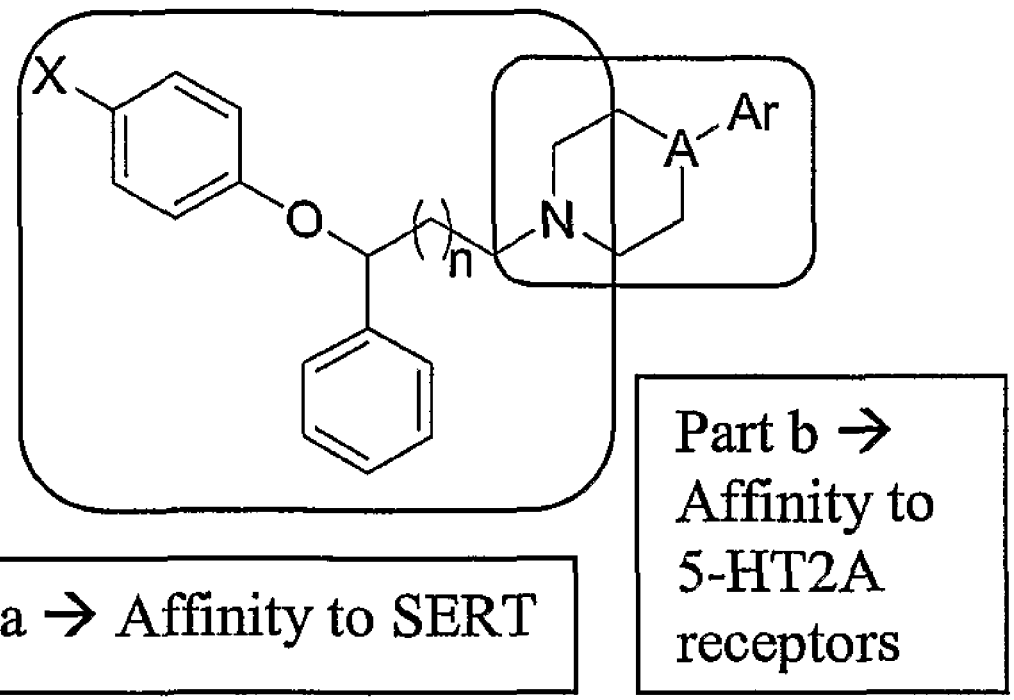
FIG. 4 shows a generalized representation of the bi-functional serotonin reuptake inhibitors.
Figure 5:
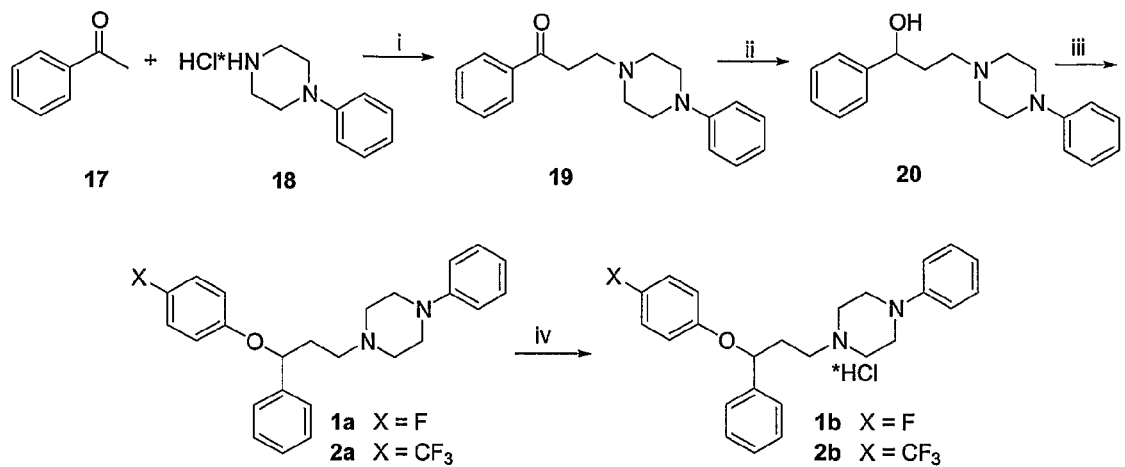
FIG. 5 shows Scheme 1, a general synthetic scheme for preparing Compounds 1-2.

The following compounds were synthesized according to Scheme 1 shown in FIG. 5 and the procedures described below:

| Cpd | Structure (Free Amine) | Cpd | Structure (Hydrochloride Salt) |
|---|---|---|---|
| 1a | | 1b | *HCl |
| 2a | | 2b | *HCl |

1. Preparation of 1-Phenyl-3-(4-phenyl-piperazin-1-yl)-propan-1-one (19)

A well-stirred mixture of acetophenone (17) (3.40 mL, 29.0 mmol), 1-phenylpiperazine hydrochloride (18) (4.48 g, 22.5 mmol), and 0.05 mL of concentrated HCl in absolute ethanol (35 mL) was heated under $N_2$ at reflux conditions. Paraformaldehyde (1.00 g, 33.3 mmol) was added in four equal portions over 40 minutes. The reaction mixture was further refluxed for 6 hours. The solution was then cooled and poured onto crushed ice. The solid was separated by filtration, dried, and re-crystallized using a small amount of aqueous ethanol (<10 mL). The solution was allowed to cool overnight and yielded 5.32 g the desired product 19 (18.1 mmol, 62%) as a white, yellow crystal. $^1$H-NMR (CDCl$_3$): δ 8.03 (2 H, d, J=7.24 Hz), 7.63 (1 H, t, J=7.37, 7.42 Hz), 7.50 (2H, t, J=7.87, 7.35 Hz), 7.31 (2H, m), 6.97 (3H, m), 3.89 (2H, t, J=6.89, 6.72 Hz), 3.62 (8H, m), 3.10 (2H, m). $^{13}$C-NMR (CDCl$_3$): δ 195.99, 149.27, 135.41, 134.24, 129.51, 128.37, 122.00, 117.43, 52.36, 51.97, 46.91, 33.14. Melting Point: 182-185° C.

2. Preparation of 1-Phenyl-3-(4-phenyl-piperazin-1-yl)-propan-1-ol (20)

To a well-stirred solution of 1-Phenyl-3-(4-phenyl-piperazin-1-yl)-propan-1-one (19) (5.32 g, 18.1 mmol) in 25 mL of methanol under $N_2$, sodium borohydride, NaBH4, (1.722 g, 45.5 mmol) was added over a period of 15 minutes at a temperature between 10 to 15° C. Care was taken to limit exposure of the NaBH$_4$ to the air. The reaction was placed at room temperature after the solution stopped bubbling and was allowed to continue stirring for 4-7 hours. The reaction mixture was poured onto crushed ice and treated with glacial acetic acid (0.2 mL). It was then extracted with ethyl acetate, EtOAc, (20 mL×4), and washed with water (10 mL×3). It was dried with anhydrous sodium sulfate and recollected by filtration. The solvent was removed under reduced pressure, and the residue obtained was triturated with methanol (3 mL). The solution remained in the refrigerator overnight. The crystallized solid was filtered and dried given 3.57 g the desired product 20 (12.0 mmol, 66.7%) as a white crystalline solid. $^1$H-NMR (CDCl$_3$): δ 7.37 (4H, m), 7.27 (3H, m), 6.92 (3H, m), 4.97 (1H, t, J=5.68, 5.75 Hz), 3.25 (4H, m), 2.72 (7H, m), 1.92 (2H, m). $^{13}$C-NMR (CDCl$_3$): δ 151.09, 144.78, 129.18, 128.07, 127.00, 125.55, 120.06, 116.29, 75.53, 57.10, 53.28, 49.29, 33.72.

Melting Point: 85-87° C.

3. Preparation of 1-[3-(4-Fluoro-phenoxy)-3-phenyl-propyl]-4-phenyl-piperazine (1a)

In a stirring solution of THF (10 mL) under $N_2$, 2 equivalents of 4-fluorophenol (1.40 g, 12.4 mmol) was added to a solution of 1-Phenyl-3-(4-phenyl-piperazin-1-yl)-propan-1-ol (20) (1.84 g, 6.22 mmol) and allowed to dissolve. 1.5 equivalents of triphenylphosphine, PPh$_3$, (2.49 g, 9.32 mmol) was then added and dissolved. After the reaction was allowed to equilibrate at a temperature between 10-15° C., 1.5 equivalents of diisopropyl azodicarboxylate, DLAD, (1.85 mL, 9.32 mmol) was added dropwise. The reaction was then allowed to return to room temperature and continued stirring for 48 hours. The solvent was then evaporated under reduced pressure and aspirated under vacuum for an extended period. Purification was performed by Flash Column Chromatography on silica gel by first washing with 500 mL of 10% EtOAc/hexanes and then extracting with 20% EtOAc/hexanes. Analytical thin-layer chromatography showed that the desired product had an R$_f$ value of approximately 0.56 when developed in 30% EtOAc/hexanes. The fractions containing the desired product were combined, and the solvent was removed under reduced pressure. 0.70 g of the product 1a (1.795 mmol, 29%) was obtained as a yellow, clear oil. $^1$H-NMR (CDCl$_3$): δ 7.29 (7H, m), 6.93 (2H, d, J=7.93 Hz), 6.86 (5H, m), 5.16 (1H, dd, J=5.00, 4.96 Hz), 3.21 (4H, t, J=4.85, 5.10 Hz), 2.60 (6H, m), 2.23 (1H, sextuplet, J=7.26, 6.75, 7.44, 6.91, 7.72 Hz), 2.02 (1H, m). $^{13}$C-NMR (CDCl$_3$): δ 155.62, 154.34, 151.28, 141.61, 129.11, 128.63, 127.69, 126.02, 119.72, 117.15, 117.04, 116.09, 115.80, 115.50, 79.34, 54.62, 53.26, 49.15, 35.96. $^{19}$F-NMR(CDCl$_3$): δ −123.77.

Elemental Analysis (%) calculated for $C_{25}H_{27}ON_2F$: C, 76.92; H, 6.92; O, 4.10;N, 7.18; F, 4.87. Found: C, 77.17; H, 7.28; O, N/A; N, 6.85; F, N/A.

4. Preparation of 1-Phenyl-4-[3-phenyl-3-(4-trifluoromethyl-phenoxy]-propyl-piperazine (2a)

In a stirring solution of THF (10 mL) under $N_2$, 2 equivalents of 4-trifluoromethyl phenol (1.873 g, 11.6 mmol) was added to a solution of 1-Phenyl-3-(4-phenyl-piperazin-1-yl)-propan-1-ol (20) (1.71 g, 5.78 mmol) and allowed to dissolve. 1.5 equivalents of triphenylphosphine, $PPh_3$, (2.293 g, 8.67 mmol) was then added and dissolved. After the reaction was allowed to equilibrate at a temperature between 10-15° C., 1.5 equivalents of diisopropyl azodicarboxylate, DLAD, (1.7 mL, 8.67 mmol) was added dropwise. The reaction was then allowed to return to room temperature and continued stirring for 48 hours. The solvent was then evaporated under reduced pressure and aspirated for an extended period. Purification was performed by Flash Column Chromatography on silica gel by first washing with 500 mL of 10% EtOAc/hexanes and then extracting with 20% EtOAc/hexanes. Analytical thin-layer chromatography showed that the desired product had an $R_f$ value of approximately 0.56 when developed in 30% EtOAc/hexanes. The fractions containing the desired product were combined, and the solvent was removed under reduced pressure. 1.38 g of the product 1a (3.17 mmol, 54%) was obtained as a yellow-orange oil. $^1$H-NMR ($CDCl_3$): δ 7.43 (2H, d, J=8.56 Hz), 7.35 (4H, m), 7.27 (3H, m), 6.91 (5H, m), 5.28 (1H, dd, J=4.90, 4.90 Hz), 3.23 (4H, t, J=4.89, 5.09 Hz), 2.66 (4H, t, J=5.87, 4.00 Hz), 2.60 (2H, t, J=7.59, 7.13 Hz), 2.27 (1H, sextuplet, J=7.34, 7.73, 6.48, 7.11, 7.58 Hz), 2.07 (1H, m). $^{13}$C-NMR ($CDCl_3$): δ 160.56, 151.12, 140.83, 129.15, 128.81, 127.94, 127.14, 126.75, 125.85, 119.97, 116.16, 115.76, 115.56, 78.62, 54.50, 53.21, 49.03, 35.72. $^{19}$F-NMR ($CDCl_3$): δ −61.52. Elemental Analysis (%) calculated for $C_{26}H_{27}ON_2F_3$: C, 70.91; H, 6.14; O, 3.64; N, 6.36; F, 12.95. Found: C, 70.94; H, 6.33; O, N/A; N, 6.17; F, N/A.

5. Preparation of the Hydrochloride salt 1b from amine 1a

To a solution of 0.164 g of product 1a (0.4 mmol) in 10 mL of stirring THF under $N_2$, 10 equivalents of 2M HCl in andydrous diethyl ether (2 mL, 4 mmol) was added at room temperature. The mixture was allowed to stir for 12 to 16 hours. The reaction mixture was then filtered and redissolved in 5 mL of anhydrous ethyl alcohol. The reaction was heated to reflux conditions for 5 to 10 minutes, and the solvent was then evaporated by reduced pressure yielding 0.083 g of the final product 1b (0.19 mmol, 46%) as a blue-green crystal. The hydrochloride salt product was confirmed by treating a sample of the product with strong base, extracting with diethyl ether, evaporating the organic layer under reduced pressure, and confirming by NMR in $CDCl_3$. The NMR data corresponded with the free amine product 1a.

Melting Point: 176-179° C.

6. Preparation of the Hydrochloride salt 2b from amine 2a

To a solution of 0.17 g of product 2a (0.4 mmol) in 10 mL of stirring THF under $N_2$, 10 equivalents of 2M HCl in andydrous diethyl ether (2 mL, 4 mmol) was added at room temperature. The mixture was allowed to stir for 12 to 16 hours. The reaction mixture was then filtered and redissolved in 5 mL of anhydrous ethyl alcohol. The reaction was heated to reflux conditions for 5 to 10 minutes, and the solvent was then evaporated by reduced pressure yielding 0.077 g of the final product 1b (0.26 mmol, 42%) as a white-yellow crystal. The hydrochloride salt product was confirmed by treating a sample of the product with strong base, extracting with diethyl ether, evaporating the organic layer under reduced pressure, and confirming by NMR in $CDCl_3$. The NMR data corresponded with the free amine product 2a.

Melting Point: 180-183° C.

EXAMPLE 3

Synthesis of Compounds 3-9

Figure 6:
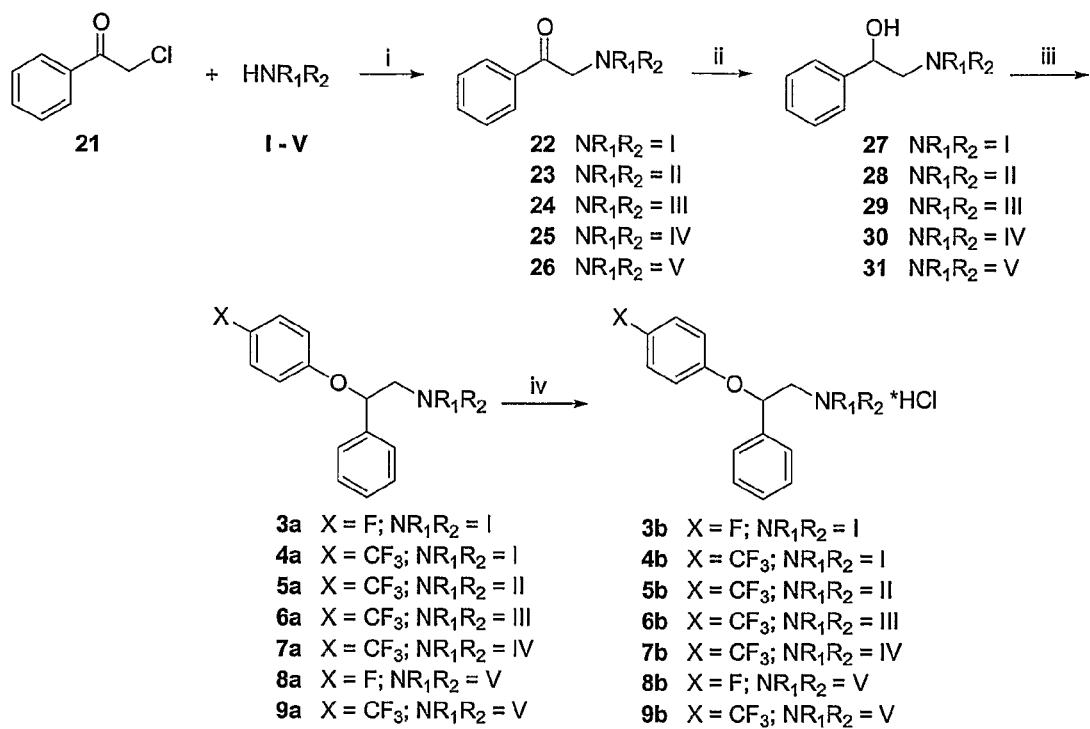
FIG. 6 shows Scheme 2, a general synthetic scheme for preparing Compounds 3-9.
Figure 6:
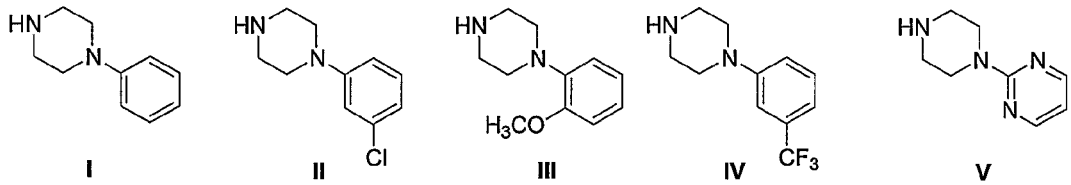

The following compounds were synthesized according to Scheme 2 shown in FIG. 6 and the procedures described below:

| Cpd | Structure (Free Amine) | Cpd | Structure (Hydrochloride Salt) |
|---|---|---|---|
| 3a | | 3b | |

-continued

| Cpd | Structure (Free Amine) | Cpd | Structure (Hydrochloride Salt) |
|---|---|---|---|
| 4a | | 4b | |
| 5a | | 5b | |
| 6a | | 6b | |
| 7a | | 7b | |
| 8a | | 8b | |

| Cpd | Structure (Free Amine) | Cpd | Structure (Hydrochloride Salt) |
|---|---|---|---|
| 9a | 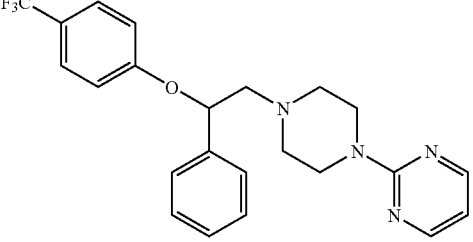 | 9b | 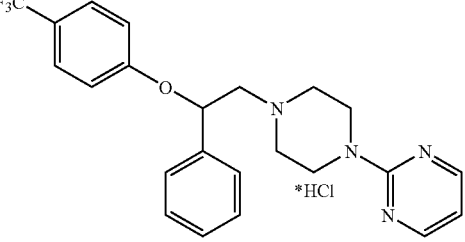 |

1. General procedure for preparation of free amines: Preparation of 1-Phenyliperazine (I)

1.05 g of 1-Phenylpiperazine hydrochloride (5.20 mmol) was added to a well stirred solution of de-ionized water (20 mL) and excess solution of 2M NaOH (100 mL). After stirring for 10 minutes under $N_2$ gas, the product was extracted with diethyl ether (30 mL×4). It was dried with anhydrous sodium sulfate, filtered, and the solvent was evaporated yielding 0.84 g of the desired free amine 1-phenylpiperazine I(5.19 mmol, 98%). $^1$H-NMR(CDCl$_3$): δ 7.27 (2H, m), 6.93 (2H, dd, J=1.07, 0.98 Hz), 6.86 (1H, tt, J=1.06, 1.04, 0.89, 0.89, 1.09, 1.06 Hz), 3.13 (4H, m), 3.04 (4H, m), 1.88 (1H, bs).

2. General Procedure for Preparation of 1-Phenyl-2-(aryl-piperazin-1-yl)-ethanones (22 to 26): Preparation of 1-Phenyl-2-(4-phenyl-piperazin-1-yl)-ethanone (22)

6.10 g of potassium carbonate, $K_2CO_3$, (6.10 mmol) was added to a dissolved, stirring solution of 1-phenylpiperazine (I) (0.84 g, 5.19 mmol) in 20 mL of acetonitrile under $N_2$. After 5 minutes, 0.80 g of 2-chloroacetophenone (21) (5.19 mmol) was added. After 5 more minutes, the solution was brought to reflux conditions (approximately 90° F.) and left for 16 hours. The solution was then allowed to cool and 50 mL of water was added. The organic layer was then extracted with dichloromethane (50 mL×3) and washed with brine solution (50 mL). It was dried with anhydrous sodium sulfate, filtered, and the solvent was evaporated. A Flash Chromatography Column was performed with 30% EtOAc/hexanes to separate the desired product. The fractions containing the product were combined, and the solvent was removed under reduced pressure. 0.87 g of the product 22 (3.107 mmol, 60%) was obtained as a yellow solid. $^1$H-NMR (CDCl$_3$): δ 8.03 (2H, d, J=8.32 Hz), 7.59 (1H, t, J=7.18, 7.57 Hz), 7.47 (2H, m), 7.28 (2H, m), 6.95 (2H, d, J=7.88 Hz), 6.87 (1H, t, J=7.29, 7.26 Hz), 3.91 (2H, s), 3.29 (4H, t, J=4.93, 5.05 Hz), 2.80 (4H, t, J=5.13, 4.82 Hz). $^{13}$C-NMR (CDCl$_3$): δ 196.03, 151.21, 135.98, 133.38, 129.13, 128.62, 128.12, 117.19, 116.19, 64.26, 53.49, 49.00. Melting Point: 104-106° C.

3. General Procedure for Preparation of 1-Phenyl-2-(aryl-piperazin-1-yl)-ethanols (27 to 31): Preparation of 1-Phenyl-2-(-phenyl-piperazin-1-yl-ethanol 27

To a well-stirred solution of 1-Phenyl-2-(4-phenyl-piperazin-1-yl)-ethanone (22) (0.87 g, 3.107 mmol) in 25 mL of methanol under $N_2$, 2.5 equivalents of sodium borohydride, $NaBH_4$, (0.294 g, 7.768 mmol) was added over a period of 15 minutes at a temperature of 10 to 15° C. Care was taken to limit exposure of the $NaBH_4$ to the air. The reaction was placed at room temperature after the solution stopped bubbling and was allowed to continue stirring for 4-7 hours. The reaction mixture was poured onto crushed ice and treated with glacial acetic acid (0.2 mL). It was then extracted with ethyl acetate, EtOAc, (20 mL×4), and washed with water (10 mL×3). It was dried with anhydrous sodium sulfate and recollected by filtration. The crystallized solid was aspirated given 0.84 g of the desired product 27 (2.979 mmol, 96%) as a white crystalline solid. $^1$H-NMR (CDCl$_3$): δ 7.39 (4H, m), 7.28 (3H, m), 6.95 (2H, dd, J=0.99, 0.83 Hz), 6.88 (1H, t, J=7.27, 7.30 Hz), 4.80 (1H, dd, J=4.67, 4.68 Hz), 3.25 (4H, dt, J=3.91, 2.47, 2.57, 3.67 Hz), 2.95 (2H, m), 2.61 (4H, m). $^{13}$C-NMR(CDCl$_3$): δ 151.16, 141.92, 129.17, 128.41, 127.60, 125.86, 119.96, 116.19, 68.78, 66.20, 53.06, 49.33. Melting Point: 107-109° C.

4. General Procedure for Preparation of 1-[2-(4-aryloxy)-2-phenyl-ethyl]-4-aryl-piperazines (3a to 9a)

a. Preparation of 1-[2-(4-Fluoro-phenoxy)-2-phenyl-ethyl]-4-phenyl-piperazine (3a)

In a stirring solution of THF (20 mL) under $N_2$, 2 equivalents of 4-trifluoromethylphenol (0.564 g, 5.035 mmol) was added to a solution of 1-Phenyl-2-(-phenyl-piperazin-1-yl)-ethanol (27) (0.71 g, 2.518 mmol) and allowed to dissolve. 1.5 equivalents of triphenylphosphine, $PPh_3$, (1.00 g, 4.574 mmol) was then added and dissolved. After the reaction was allowed to equilibrate at a temperature between 10-15° C., 1.5 equivalents of diisopropyl azodicarboxylate, DIAD, (0.75 mL, 4.574 mmol) was added dropwise. The reaction was then allowed to return to room temperature and continued stirring for 48 hours. The solvent was then evaporated under reduced pressure and aspirated for an extended period. Purification was performed by Flash Column Chromatography on silica gel by first washing with 500 mL of 10% EtOAc/hexanes and then extracting with 20% EtOAc/hexanes. Analytical thin-layer chromatography showed that the desired product had an $R_f$ value of approximately 0.50 when developed in 30% EtOAc/hexanes. The fractions containing the desired product were combined, and the solvent was removed under reduced pressure. 0.80 g of the product 1a (2.128 mmol, 36%) was obtained as a white solid. $^1$H-NMR (CDCl$_3$): δ 7.35 (4H, m), 7.26 (3H, m), 6.95 (2H, dd, J=0.92, 0.81 Hz), 6.84 (5H, m), 5.29 (1H, dd, J=3.10, 3.09 Hz), 3.21 (4H, t, J=5.04, 4.99 Hz), 3.06 (1H, dd, J=8.48, 8.49 Hz), 2.85 (2H, m), 2.74 (3H, m). $^{13}$C-NMR (CDCl$_3$): δ 155.72, 153.92, 151.31, 140.35, 129.10, 128.67, 127.68, 126.13, 119.71, 117.28, 117.17, 116.05, 115.85, 115.54, 79.71, 65.39, 53.63, 49.24. $^{19}$F-NMR (CDCl$_3$): δ −123.53. Melting Point: 80-82° C.

Elemental Analysis (%) calculated for $C_{24}H_{25}ON_2F$: C, 76.60; H, 6.65; O, 4.25; N, 7.45; F, 5.05. Found: C, 76.58; H, 6.75; O, N/A; N, 7.46; F, N/A.

b. Preparation of 1-Phenyl-4-[2-phenyl-2-(4-trifluoromethyl-phenoxy)-ethyl]-piperazine In a stirring solution of THF (20 mL) under $N_2$, 2 equivalents of 4-fluorophenol (0.965 g, 5.985 mmol) was added to a solution of 1-Phenyl-2-(-phenyl-piperazin-1-yl)-ethanol (27) (0.84 g, 2.979 mmol) and allowed to dissolve. 1.5 equivalents of triphenylphosphine, $PPh_3$, (1.172 g, 4.468 mmol) was then added and dissolved. After the reaction was allowed to equilibrate at a temperature between 10-15° C., 1.5 equivalents of diisopropyl azodicarboxylate, DIAD, (0.88 mL, 4.468 mmol) was added dropwise. The reaction was then allowed to return to room temperature and continued stirring for 48 hours. The solvent was then evaporated under reduced pressure and aspirated for ail extended period. Purification was performed by Flash Column Chromatography on silica gel by first washing with 500 mL of 10% EtOAc/hexanes and then extracting with 20% EtOAc/hexanes. Analytical thin-layer chromatography showed that the desired product had an $R_f$ value of approximately 0.48 when developed in 30% EtOAc/hexanes. The fractions containing the desired product were combined, and the solvent was removed under reduced pressure. 0.51 g of the product 1a (1.197 mmol, 40%) was obtained as a clear yellow oil. $^1$H-NMR ($CDCl_3$): δ 7.44 (2H, d, J=8.45 Hz), 7.36 (4H, m), 7.27 (3H, m), 6.92 (4H, m), 6.85 (1H, t, J=7.28, 7.30 Hz), 5.42 (1H, dd, J=3.19, 3.20 Hz), 3.19 (4H, t, J=5.04, 4.99 Hz), 3.08 (1H, dd, J=8.33, 8.36 Hz), 2.78 (5H, m). $^{13}$C-NMR ($CDCl_3$): δ 160.25, 151.30, 139.74, 129.12, 128.82, 128.06, 126.82, 126.77, 126.72, 126.01, 123.23, 119.78, 116.09, 115.93, 79.22, 65.66, 53.30, 49.27. $^{19}$F-NMR ($CDCl_3$): δ −61.53. Elemental Analysis (%) calculated for $C_{25}H_{25}ON_2F_3$: C, 70.42; H, 5.87; O, 3.76; N, 6.57; F, 13.38. Found: C, 70.51; H, 5.94; O, N/A; N, 6.57; F, N/A.

5. General Procedure for Preparation of Hydrochloride Salts (3b to 9b) from 3a to 9a a. Preparation of the Hydrochloride Salt 3b from the Free Amine Product 3a

To a solution of 0.80 g of product 1a (2.12 mmol) in 10 mL of stirring THF under $N_2$, 10 equivalents of 2M HCl in andydrous diethyl ether (1 mL, 21.2 mmol) was added at room temperature. The mixture was allowed to stir for 12 to 16 hours. The reaction mixture was then filtered and redissolved in 10 mL of anhydrous ethyl alcohol. The reaction was heated to reflux conditions for 5 to 10 minutes, and the solvent was then evaporated by reduced pressure yielding 0.66 g of the final product 1b (1.602 mmol, 75%) as a white-cream solid. The hydrochloride salt product was confirmed by treating a sample of the product with strong base, extracting with diethyl ether, evaporating the organic layer under reduced pressure, and confirming by NMR in $CDCl_3$. The NMR data corresponded with the free amine product 3a.

Melting Point: 195-198° C.

b. Preparation of the Hydrochloride Salt 4b from the Free Amine Product 4a

To a solution of 0.96 g of product 1a (2.25 mmol) in 15 mL of stirring TBF under $N_2$, 10 equivalents of 2M HCl in andydrous diethyl ether (12 mL, 22.5 mmol) was added at room temperature. The mixture was allowed to stir for 12 to 16 hours. The reaction mixture was then filtered and redissolved in 10 mL of anhydrous ethyl alcohol. The reaction was heated to reflux conditions for 5 to 10 minutes, and the solvent was then evaporated by reduced pressure yielding 0.85 g of the final product 1b (1.839 mmol, 82%) as a blue-green solid. The hydrochloride salt product was confirmed by treating a sample of the product with strong base, extracting with diethyl ether, evaporating the organic layer under reduced pressure, and confirming by NMR in $CDCl_3$. The NMR data corresponded with the free amine product 4a.

Melting Point: 161-163° C.

EXAMPLE 4

Synthesis of Compounds 10-12

Figure 7:
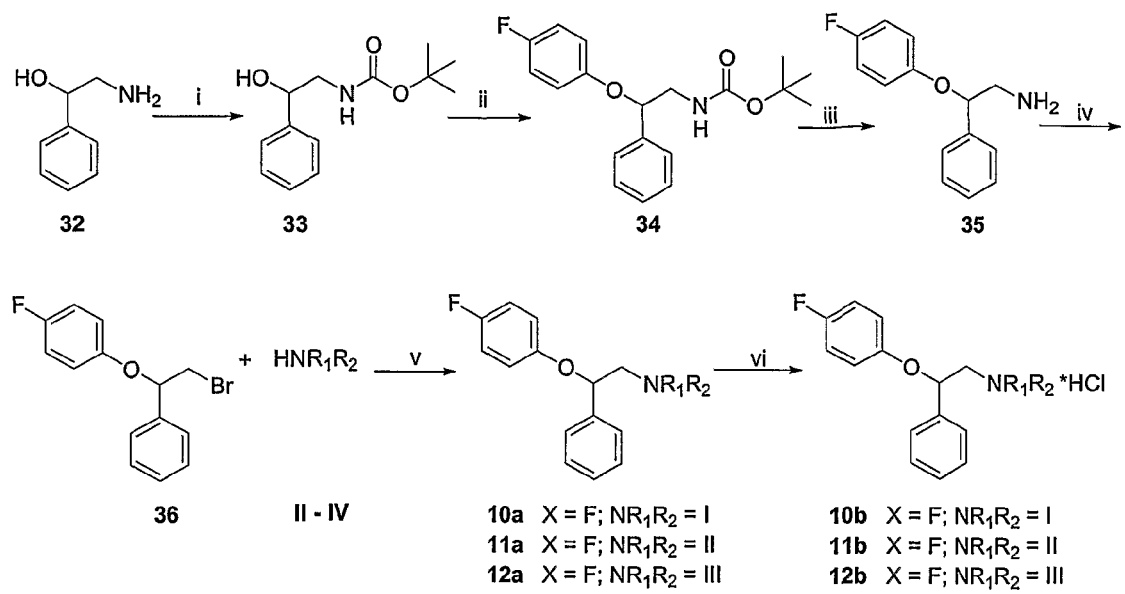
FIG. 7 shows Scheme 3, a general synthetic scheme for preparing Compounds 10-12.
Figure 7:
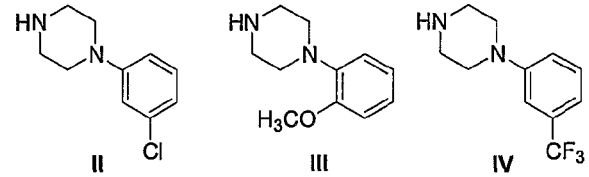

The following compounds were synthesized according to Scheme 3 shown in FIG. 7 and the procedures described below:

| Cpd | Structure (Free Amine) | Cpd | Structure (Hydrochloride Salt) |
|---|---|---|---|
| 10a | [structure of free amine with F-phenyl, O, phenyl, piperazine, chlorophenyl] | 10b | [structure of hydrochloride salt with F-phenyl, O, phenyl, piperazine, chlorophenyl, *HCl] |

-continued

| Cpd | Structure (Free Amine) | Cpd | Structure (Hydrochloride Salt) |
|---|---|---|---|
| 11a | [structure: 4-fluorophenoxy-phenylethyl-piperazine-(2-methoxyphenyl)] | 11b | [structure: 4-fluorophenoxy-phenylethyl-piperazine-(2-methoxyphenyl) *HCl] |
| 12a | [structure: 4-fluorophenoxy-phenylethyl-piperazine-(3-trifluoromethylphenyl)] | 12b | [structure: 4-fluorophenoxy-phenylethyl-piperazine-(3-trifluoromethylphenyl) *HCl] |

1. Preparation of (2-hydroxy-2-phenylethyl)-carbamic acid tert-butyl ester (33)

To a well-stirred solution of 2-amino-1-phenylethanol (32) (5.05 g, 36.8 mmol) in anhydrous DMF (50 mL) under $N_2$ at 25° C. was added 1.5 molar equivalents of di-tert-butyl dicarbonate (t-boc anhydride) (13.24 g, 60.7 mmol). After dissolution of the t-boc anhydride, the mixture was brought to 50° C. for approximately 15 minutes and then allowed to cool to 25° C. After stirring overnight (8-12 hours), ethyl acetate (EtOAc) was added to the reaction mixture. Water was then added, and the organic layer was extracted three times with water and subsequently dried over anhydrous magnesium sulfate ($MgSO_4$). The mixture was then filtered and the solvent removed under reduced pressure. The resulting residue was suspended in a minimal amount of EtOAc and heated to 55-60° C. until completely dissolved. The mixture was allowed to cool overnight, remaining undisturbed, and afforded the desired product 33 (6.73 g, 28.4 mmol, 78%) as translucent, slightly yellow crystals. $^1$H-NMR ($CDCl_3$): δ 7.31 (5H, m), 4.97 (1H, bs), 4.82 (1H, dd, J=3.9, 3.7 Hz), 3.47 (1H, ddd, J=14.0, 6.5, 3.2 Hz), 3.27 (1H, dd, J=7.8, 5.4 Hz), 3.22 (1H, dd, J=8.6, 6.1 Hz), 1.71 (1H, bs), 1.44 (9H, s). $^{13}$C-NMR ($CDCl_3$): δ 157.0 (faint), 142.2, 128.9, 128.9, 128.2, 126.3, 126.3, 80.3, 74.4, 48.8, 28.8, 28.8, 28.8. Melting point: 123-124° C.

2. Preparation of [2-(4-fluorophenoxy)-2-phenylethyl]-carbamic acid tert-butyl ester (34)

To a well-stirred solution of 33 (6.73 g, 28.4 mmol) in anhydrous THF (40 mL) under $N_2$ at 25° C. is added 2 molar equivalents (eq.) of 4-fluorophenol (6.55 g, 58.4 mmol). After complete dissolution of the 4-fluorophenol, 1.5 eq. of triphenylphosphine ($PPh_3$) (11.68 g, 44.5 mmol) was added to the mixture and allowed to completely dissolve. The reaction vessel was then cooled in an ice bath to 0° C. After 20 minutes, 1.5 eq. of diethylazodicarboxylate (DEAD) (7.96 g, 45.7 mmol) was slowly added dropwise to the stirring mixture. The reaction vessel was subsequently allowed to return to room temperature (25° C.). After stirring overnight (8-12 hours), the triphenylphosphine salts formed during the reaction were removed by filtration and the solvent evaporated under reduced pressure. The residue was adsorbed onto silica gel and purified by flash column chromatography (silica gel, 5:95 EtOAc/hexanes) which afforded the desired intermediate 34 (4.04 g, 12.2 mmol, 43%) as a white solid. $^1$H-NMR ($CDCl_3$): δ 7.34 (1H, d, J=5.4 Hz), 7.33 (1H, d, J=8.0 Hz), 7.31 (1H, d, J=4.8 Hz), 7.30 (1H, d, J=7.1 Hz), 7.27 (1H, d, J=4.2 Hz), 6.89 (1H, d, J=10.6 Hz), 6.85 (1H, d, J=9.0 Hz), 6.78 (1H, d, J=9.2 Hz), 6.76 (1H, d, J=9.2 Hz), 5.16 (1H, dd, J=8.5, 3.4 Hz), 5.02 (1H, bs), 3.63 (1H, ddd, J=14.4, 8.0, 3.7 Hz), 3.39 (1H, ddd, J=13.3, 8.3, 4.6 Hz), 1.43 (9H, s). $^{13}$C-NMR ($CDCl_3$): δ 158.7, 156.0, 155.8, 153.8, 138.5, 128.7, 128.1, 128.1, 126.1, 126.1, 117.0, 116.9, 115.9, 115.6, 80.0, 68.1, 47.2, 28.4, 28.4, 28.4. $^{19}$F-NMR ($CDCl_3$): δ −123.8. Melting point: 98-102° C.

3. Preparation of 2-(4-fluorophenoxy)-2-phenyl-ethylamine (35)

A 30 mL volume of 4 N HCl in dioxane was prepared by adding dropwise 10 mL of 12 N (i.e.; concentrated) hydrochloric acid to 20 mL of well-stirred amount of 1,4-dioxane. The t-boc protected 4-fluorophenyl ether intermediate 34 (4.04 g, 12.2 mmol) was dissolved in a minimal amount of 1,4-dioxane. The 4 N HCl was then added dropwise to the reaction vessel at 25° C. over approximately a 10 minute period. After 90 minutes, a saturated solution of sodium bicarbonate ($NaHCO_3$) was added to the reaction mixture. The aqueous layer was washed with three separate 30 mL portions of $CH_2Cl_2$. The combined organic layers were then dried over anhydrous $MgSO_4$ and filtered. Purification was performed by flash column chromatography (on silica gel) starting with 100% EtOAc until any remaining starting material had eluted; then the polarity of the eluent was increased using 30:70 methanol/EtOAc. Analytical thin-layer chromatography showed that the desired product had an $R_f$ value of approximately 0.4 when developed in 30:70 methanol/EtOAc. Fractions containing the desired product were combined and the solvent was removed under reduced pressure. The resultant residue after solvent evaporation was re-suspended in $CH_2Cl_2$ and filtered. The solvent from the filtrate was evaporated under reduced pressure and afforded the desired free amine 5 (1.80 g, 7.8 mmol, 64%) as a slightly yellow oil. $^1$H-NMR ($CDCl_3$): δ 7.28 (5H, m), 6.86 (1H, d, J=9.3 Hz), 6.83 (1H, d, J=8.0 Hz), 6.79 (1H, d, J=9.3 Hz), 6.78 (1H, d, J=9.4 Hz), 5.06 (1H, dd, J=7.1, 4.4 Hz), 3.14 (1H, d, J=6.8 Hz), 3.12 (1H, d, J=7.7 Hz), 2.35 (2H, bs). $^{13}$C-NMR ($CDCl_3$): δ 158.6, 156.0, 154.0, 139.0, 128.7, 128.0, 126.1, 126.1, 117.0, 116.9, 115.8, 115.6, 82.3, 49.0. $^{19}$F-NMR ($CDCl_3$): δ −124.0.

4. 2-(4-fluorophenoxy)-2-phenyl-ethyl bromide (36)

To a rapidly stirred solution of 1.1 eq. of $TiBr_4$ (3.15 g, 8.67 mmol) in 40 mL of DMF at 25° C. under $N_2$ was added dropwise 1.1 eq. of t-butyl nitrite (1.2 mL of 90% t-butyl nitrite, d=0.86, 8.6 mmol) dissolved in approx. 5 mL of DMF. Upon addition of the t-butyl nitrite, a color change from reddish orange to orange-yellow was observed. The primary amine starting material 35 (180 g, 7.8 mmol) was dissolved in approximately 5 mL of DMF and added dropwise to the reaction flask over a 20-minute period. Gas evolution was observed during addition of the amine starting material and was complete within approximately 5 minutes following its complete addition. After complete gas evolution, the reaction mixture was added to 150 mL of 20% aqueous hydrochloric acid (20% aq. HCl) and extracted with four 30 mL portions of ethyl ether. The combined organic layers were subsequently dried over anhydrous $MgSO_4$. The solvent was then removed under reduced pressure. Analytical thin-layer chromatography (TLC) indicated that the desired product had an $R_f$ value of approx. 0.85 when developed in 30:70 EtOAc/hexanes. Purification was performed using flash column chromatography (silica gel, 100% hexanes) to isolate the desired bromide product 36 (0.74 g, 2.6 mmol, 33%) as a yellow oil. $^1$H-NMR ($CDCl_3$): δ 7.37 (5H, m), 6.89 (1H, d, J=8.0 Hz), 6.87 (1H, d, J=8.0 Hz), 6.83 (1H, d, J=4.5 Hz), 6.81 (1H, d, J=4.6 Hz), 5.22 (1H, dd, J=8.4, 4.0 Hz), 3.72 (1H, dd, J=10.9, 8.4 Hz), 3.61 (1H, dd, J=10.9, 4.0 Hz). $^{13}$C-NMR ($CDCl_3$): δ 159.6, 156.5, 154.3, 154.3, 138.9, 129.3, 129.2, 126.8, 118.0, 117.9, 116.4, 116.1, 81.7, 36.4. $^{19}$F-NMR ($CDCl_3$): δ −123.2.

5. Preparation of 1-(3-chlorophenyl)-4-[2-(4-fluorophenoxy)-2-phenylethyl]1-piperazine (10a)

To a well-stirred solution of approx. 1.1 eq. of 1-(3-chlorophenyl)-piperazine (II) (0.26 g, 1.3 mmol) in 20 mL DMF at 25° C. under $N_2$ and fitted with a reflux condenser was added a minimum of 1-25 eq. of anhydrous $K_2CO_3$ (0.27 g, 1.9 mmol). The starting material 36 (0.24 g, 0.83 mmol) was dissolved in a small amount of DMF (approx. 5 mL) and added to the reaction mixture. After stirring for 10 minutes, the reaction mixture was then brought to reflux temperature and allowed to reflux under an inert atmosphere for 16 hours. Upon completion of the reaction, water was added and the reaction mixture was extracted with four 30 mL portions of $CH_2Cl_2$. The organic layers were combined and dried over anhydrous $MgSO_4$. The solvent was removed under reduced pressure and the residue was adsorbed onto silica gel and purified via flash column chromatography. Analytical thin layer chromatography (TLC) indicated the desired product had an $R_f$ value of approx. 0.75 when developed in 30:70 EtOAc/hexanes. Purification via flash column chromatography (on silica gel) was performed with 500 ml of hexanes until any remaining starting material had completely eluted; then the polarity of the eluent mixture was increased to 10:90 EtOAc/hexanes to afford the desired product 10a (0.24 g, 0.57 mmol, 69%) as an opalescent oil. $^1$H-NMR ($CDCl_3$): δ 7.31 (5H, m), 7.15 (1H, dd, J=8.1, 8.0 Hz), 6.82 (7H, m), 5.27 (1H, dd, J=8.4, 3.2 Hz), 3.19 (4H, dd, J=5.1, 5.0 Hz), 3.04 (1H, dd, J=13.8, 8.5 Hz), 2.82 (2H, ddd, J=9.4, 8.1, 5.0 Hz), 2.73 (3H, ddd, J=6.9, 6.9, 3.1 Hz).

$^{13}$C-NMR($CDCl_3$): δ 154.3, 152.7, 147 (faint), 140.6, 135.3, 130.4, 129.1, 129.1, 128.3, 126.5, 126.5, 119.7, 117.6, 117.5, 116.3, 116.1, 116.0, 114.3, 80.1, 65.7, 53.8, 53.8, 49.2, 49.2. $^{19}$F-NMR ($CDCl_3$): δ −124.0. HRMS (EI) M+calculated for $C_{24}H_{24}ClFN_2O$: 410.91, found 410.16.

Elemental analysis (%) calculated for $C_{24}H_{24}ClFN_2O$: C, 70.15; H, 5.89; N, 6.82; F, 4.62; Cl, 8.63. Found: C, 70.43; H, 6.02; N, 6.75; F, n/a; Cl, n/a.

6. Preparation of 1-[2-(4-fluorophenoxy)-2-phenylethyl]-4-(2-methoxyxhenyl)-piperazine (11a)

a. Formation of the free base form of 1-(2-methoxyphenyl)-piperazine. The free base form of 1-(2-methoxyphenyl)-piperazine was formed by dissolving a liberal amount of the corresponding hydrochloride salt (III) in deionized water and adding an excess of 2 M aqueous NaOH. After 10 minutes, the aqueous mixture was extracted with four 30 mL portions of ethyl ether. The combined organic layers were dried over anhydrous $MgSO_4$ and the solvent was removed under reduced pressure. The secondary amine (free base form) of 1-(2-methoxyphenyl)-piperazine was isolated as an off-white solid and confirmed via NMR spectroscopy. $^1$H-NMR ($CDCl_3$): δ 7.07 (1H, ddd, J=9.1, 8.0, 4.5 Hz), 6.94 (1H, d, J=8.6 Hz), 6.93 (1H, d, J=4.1 Hz), 6.89 (1H, d, J=7.7 Hz), 3.87 (3H, s), 3.38 (4H, d, J=15.3 Hz), 3.38 (2H, d, J=4.0 Hz), 3.14 (1H, bs), 2.85 (1H, bs), 1.83 (1H, s). $^{13}$C-NMR ($CDCl_3$): δ 152.2, 141.7, 122.7, 120.9, 118.1, 111.1, 55.2, 52.0, 52.0, 46.3, 46.3 Melting point: 180-183° C. (dec.)

b. Formation the coupled product 11a. To a well-stirred solution of approx. 1.6 eq. of 1-(2-methoxyphenyl)-piperazine (III) (0.34 g, 1.78 mmol) in 20 mL DMF at 25° C. under $N_2$ and fitted with a reflux condenser was added a minimum of 1.25 eq. of anhydrous $K_2CO_3$ (0.34 g, 2.45 mmol). The starting material 36 (0.245 g, 0.83 mmol) was dissolved in a small amount of DMF (approx. 5 mL) and added to the reaction mixture. After stirring for 10 minutes, the reaction mixture was then brought to reflux temperature and allowed to reflux under an inert atmosphere for 16 hours. Upon completion of the reaction, water was added and the reaction mixture was extracted with four 30 mL portions of $CH_2Cl_2$. The organic layers were combined and dried over anhydrous $MgSO_4$. The solvent was removed under reduced pressure and the residue was adsorbed onto silica gel and purified via flash column chromatography. Analytical thin layer chromatography (TLC) indicated the desired product had an $R_f$ value of approx. 0.7 when developed in 30:70 EtOAc/hexanes. The flash column chromatography (on silica gel) was performed with 500 mL of hexanes until any remaining starting material had completely eluted; then the polarity of the eluent mixture was increased to 10:90 EtOAc/hexanes to afford the desired product 11a (0.114 g, 0.28 mmol, 34%) as an opalescent oil. $^1$H-NMR ($CDCl_3$): δ 7.32 (5H, m), 6.9 (8H, m), 5.30 (1H, dd, J=8.5, 3.1 Hz), 3.86 (3H, s), 3.1 (5H, dd, J=13.7, 8.5 Hz), 2.8

(5H, m). $^{13}$C-NMR (CDCl$_3$): δ 152.6, 152.6, 141.7, 140.9, 129.1, 129.1, 129.1, 128.2, 126.5, 126.5, 123.3, 121.4, 118.6, 117.7, 117.6, 116.2, 116.0, 111.5, 79.9, 66.0, 55.7, 55.7, 54.2, 51.1, 51.1. $^{19}$F-NMR (CDCl$_3$): δ −124.2. HRMS (EI) M+calculated for C$_{25}$H$_{27}$FN$_2$O$_2$: 406.49; found 406.21. Elemental analysis (%) calculated for C$_{25}$H$_{27}$FN$_2$O$_2$: C, 73.87; H, 6.69; F, 4.67; N, 6.89. Found: C, 73.84; H, 6.95; F, n/a; N, 6.92.

7. Preparation of 1-[2-(4-fluorophenoxy)-2-phenylethyl]-4-(3-trifluoromethylphenyl)-piperazine (12a)

To a well-stirred solution of approx. 1.1 eq. of m-trifluoromethylphenyl-piperazine (IV) (0.44 g, 1.9 mmol) in 20 mL DMF at 25° C. under N$_2$ and fitted with a reflux condenser was added a minimum of 1.25 eq of anhydrous K$_2$CO$_3$ (0.33 g, 2.4 mmol). The starting material 36 (0.41 g, 1.4 mmol) was dissolved in a small amount of DMF (approx. 5 mL) and added to the reaction mixture. After stirring for 10 minutes, the reaction mixture was then brought to reflux temperature and allowed t( reflux under an inert atmosphere for 16 hours. Upon completion of the reaction, water was added and the reaction mixture was extracted with four 30 mL portions of CH$_2$Cl. The organic layers were combined and dried over anhydrous MgSO$_4$. The solvent was removed under reduced pressure and the residue was adsorbed onto silica gel and purified via flash column chromatography. Analytical thin layer chromatography (TLC) indicated the desired product had an R$_f$ value of approx. 0.75-0.8 when developed in 30:70 EtOAc/hexanes. Purification via flash column chromatography (on silica gel) was performed with 500 mL of hexanes until any remaining starting material had completely eluted; then the polarity of the eluent mixture was increased to 10:90 EtOAc/hexanes to afford the desired product 12a (0.11 g, 0.25 mmol, 18%) as an opalescent oil. $^1$H-NMR (CDCl$_3$): δ 7.32 (6H, m), 7.09 (1H, d, J=7.6 Hz), 7.07 (1H, d, J=7.8 Hz), 7.05 (1H, d, J=7.0 Hz), 6.88 (1H, d, J=9.3 Hz), 6.85 (1H, d, J=8.2 Hz), 6.80 (1H, d, J=9.3 Hz), 6.79 (1H, d, J=9.3 Hz), 5.28 (1H, dd, J=8.4, 3.3 Hz), 3.24 (4H, dd, J=5.0, 5.0 Hz), 3.05 (1H, dd, J=13.9, 8.5 Hz), 2.84 (2H, ddd, J=10.8, 5.2, 5.2 Hz), 2.74 (3H, m). $^{13}$C-NMR (CDCl$_3$): δ 152 (faint), 151 (faint), 145 (faint), 140 (faint), 129.5, 129.5, 128.7, 128.7, 127.9, 126.1, 126.1, 118.6, 117.2, 117.1, 115.8, 115.8, 115.6, 112, 112, 79.7, 65.2, 53.4, 53.4, 48.7, 48.7. $^{19}$F-NMR(CDCl$_3$): δ −63.1, −123.5 HRMS (EI) M+calculated for C$_{25}$H$_{24}$F$_4$N$_2$O: 444.46, found 444.18. Elemental analysis (%) calculated for C$_{25}$H$_{24}$F$_4$N$_2$O: C, 67.56; H, 5.44; F, 17.10; N, 6.30. Found: C, 68.20; H, 5.82; F, 15.22; N, 5.90.

8. Formation of the hydrochloride salt 10b from piperazinyl-containing base 10a To a well-stirred solution of 10a (0.235 g, 0.57 mmol) in 30 mL of anhydrous THF was added 10 eq. of 2M HCl in anhydrous diethyl ether (3 mL, 6.0 mmol) at 25° C. under N$_2$. The mixture was allowed to stir for approx. 12 to 16 hours. Upon completion of the reaction, the reaction mixture was filtered and the filtered residue was washed with freshly distilled CH$_2$Cl$_2$. The solute was then allowed to dry and was subsequently re-dissolved in approx. 5 mL of anhydrous EtOH. The resulting solution was refluxed briefly for 5-10 minutes and the solvent then was removed under reduced pressure. The remaining solid was placed under vacuum until all residual solvent was removed affording the desired hydrochloride salt 10b as a greenish crystalline solid (0.17 g, 0.39 mmol, 68%). Confirmation of the HCl salt 10b was made by treating a small amount of the final product with strong base, extracting with ethyl ether, removing the organic solvent under reduced pressure, and confirming via NMR using CDCl$_3$. NMR data corresponded with those results previously reported for the free base form 10a. TLC was also performed (30:70 EtOAc/hexanes) and the R$_f$ value of approx. 0.75 matched that of 10a. Reverse phase TLC was performed on the HCl salt 10b and R$_f$ values of 0.3 in 100% CH$_3$CN and 0.8 in 2:98 H$_2$O/ CH$_3$CN were recorded, respectively.

9. Formation of the hydrochloride salt 11b from piperazinyl-containing base 11a To a well-stirred solution of 11a (0.114 g, 0.28 mmol) in 30 mL of anhydrous THF was added 10 eq. of 2 M HCl in anhydrous diethyl ether (1.6 mL, 3.2 mmol) at 25° C. under N$_2$. The mixture was allowed to stir for approx. 12 to 16 hours. Upon completion of the reaction, the reaction mixture was filtered and the filtered residue was washed with freshly distilled CH$_2$Cl$_2$. The solute was then allowed to dry and was subsequently re-dissolved in approx. 5 mL of anhydrous EtOH. The resulting solution was refluxed briefly for 5-10 minutes and the solvent was then removed under reduced pressure. The remaining solid was placed under vacuum until all residual solvent was removed affording the desired hydrochloride salt 11b as a white crystalline solid (0.0112 g, 0.025 mmol, 9%), albeit in low yield. Confirmation of the HCl salt 11b was made by treating a small amount of the final product with strong base, extracting with ethyl ether, removing the organic solvent under reduced pressure, and confirming via NMR using CDCl$_3$. NMR data corresponded with those results previously reported for the freebase form 11a. TLC was also performed (30:70 EtOAc/hexanes) and the R$_f$ value of approx. 0.7 matched that of 11a. Reverse phase TLC was performed on the HCl salt 11b and R$_f$ values of 0.25 in 100% CH$_3$CN and 0.75 in 2:98 H$_2$O/ CH$_3$CN were recorded, respectively.

10. Formation of the hydrochloride salt 12b from piperazinyl-containing base 12a To a well-stirred solution of 12a (0.11 g, 0.25 mmol) in 30 mL of anhydrous TBF was added 10 eq. of 2 M HCl in anhydrous diethyl ether (1.4 mL, 2.8 mmol) at 25° C. under N$_2$. The mixture was allowed to stir for approx. 12 to 16 hours. Upon completion of the reaction, the reaction mixture was filtered and the filtered residue was washed with freshly distilled CH$_2$Cl$_2$. The solute was then allowed to dry and was subsequently re-dissolved in approx. 5 mL of anhydrous EtOH. The resulting solution was refluxed briefly for 5-10 minutes and the solvent then was removed under reduced pressure. The remaining solid was placed under vacuum until all residual solvent was removed affording the desired hydrochloride salt 12b (0.0496 g, 0.103 mmol, 42%). Confirmation of the HCl salt 12b was made by treating a small amount of the final product with strong base, extracting with ethyl ether, removing the organic solvent under reduced pressure, and confirming via NMR using CDCl$_3$. NMR data corresponded with those previously reported for the free base form 12a. TLC was also performed (30:70 EtOAc/hexanes) and the R$_f$ value of approx. 0.75-0.8 matched that of 12a. Reverse phase TLC was performed on the HCl salt 12b and R$_f$ values of 0.35 in 100% CH$_3$CN and 0.85 in 2:98 H$_2$O/ CH$_3$CN were recorded, respectively.

EXAMPLE 5

Synthesis of Compounds 13-16

Figure 8:
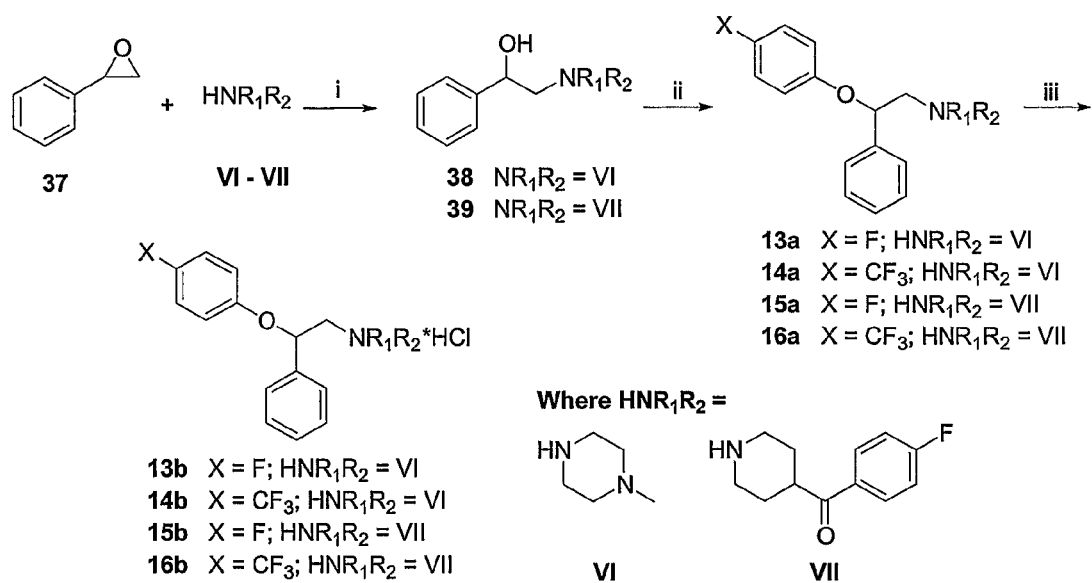
FIG. 8 shows Scheme 4, a general synthetic scheme for preparing Compounds 13-16.

The following compounds were synthesized according to Scheme 4 shown in FIG. 8 and the procedures described below:

| Cpd | Structure (Free Amine) | Cpd | Structure (Hydrochloride Salt) |
|---|---|---|---|
| 13a | [4-fluorophenoxy-2-phenylethyl-4-methylpiperazine structure] | 13b | [4-fluorophenoxy-2-phenylethyl-4-methylpiperazine · HCl structure] |
| 14a | [4-trifluoromethylphenoxy-2-phenylethyl-4-methylpiperazine structure] | 14b | [4-trifluoromethylphenoxy-2-phenylethyl-4-methylpiperazine · HCl structure] |
| 15a | [4-fluorophenoxy-2-phenylethyl-piperidine-4-(4-methylbenzoyl) structure] | 15b | [4-fluorophenoxy-2-phenylethyl-piperidine-4-(4-methylbenzoyl) · HCl structure] |
| 16a | [4-trifluoromethylphenoxy-2-phenylethyl-piperidine-4-benzoyl structure] | 16b | [4-trifluoromethylphenoxy-2-phenylethyl-piperidine-4-benzoyl · HCl structure] |

(4×100 mL) and the organic layer washed with brine. The organic layer was dried over $Na_2SO_4$ and the solvent evaporated. The product was purified using flash chromatography, eluting pure ethyl acetate until any remaining starting material had been recovered and then increasing the polarity of the solvent using 30:70 methanol/ethyl acetate. The product 38 (5.66 g, 25.73 mmol, 31%) was afforded as a white-pink solid. $^1$H-NMR (CDCl$_3$): δ 7.36 (5H, m), 4.74 (1H, dd, J=4.05, 4.06 Hz), 4.00 (1H, b), 2.79 (2H, b), 2.51 (8H, m), 2.31 (3H, s).

1. General Procedure for preparation of 2-amino-1-phenyl ethanols (38 and 39): Synthesis of 2-(4-Methyl-piperazin-1-yl)-1-phenyl-ethanol (38)

To a solution of 3.0 equivalents of 1-methylpiperazine (VI) (25.0 g, 24.96 mmol) in 100 mL was added 3.0 equivalents of K2CO3 (34.5 g, 24.96 mmol) and the solution allowed to stir for 10 minutes. After that time, styrene oxide 37 (100 g, mmol) was added to the solution and the reaction mixture was refluxed overnight. After 16 h, the reaction mixture was cooled to room temperature and quenched with 200 mL of water. The reaction was extracted with dichloromethane

2. General Procedure for Preparation of 1-[2-(4-aryloxy)-2-phenyl-ethyl]-4-aryl-piperazines (13a to 16a)

a. Preparation of 1-[2-(4-Fluoro-phenoxy)-2-phenyl-ethyl]-4-methyl-piperazine (13a)

2-(4-Methyl-piperazin-1-yl)-1-phenyl-ethanol (38) (2.0 g, 9.09 mmol) was dissolved in 50 mL of THF. 4-fluorophenol was added to the solution and then triphenylphosphine. After complete dissolution, the mixture was cooled to 0° C. and after 10 minutes DIAD was added dropwise. Ice-bath was removed and the reaction mixture was stirred at room temperature for 48 hours. The product was purified using flash chromatography, eluting pure ethyl acetate to recover any starting materials. Polarity of the solvent was then increased using 30:70 methanol/ethyl acetate. The product 13a (2.18 g, 6.94 mmol, 76%) was afforded as a orange-brown oil. $^1$H-NMR (CDCl$_3$): δ 7.33 (5H, m), 6.80 (4H, m), 5.21 (1H, dd, J=3.08, 3.07 Hz), 3.00 (1H, dd, J=8.49, 8.48), 2.67 (5H, b), 2.45 (4H, b), 2.27 (3H, s).

b. Preparation of 1-Methyl-4-[2-phenyl-2-(4-trifluoromethyl-phenoxy)-ethyl]-piperazine (14a)

2-(4-Methyl-piperazin-1-yl)-1-phenyl-ethanol (38) (2.0 g, 9.09 mmol) was dissolved in 50 mL of THF. 4-trifluoromethyl phenol was added to the solution and then triphenylphosphine. After complete dissolution, the mixture was cooled to 0° C. and after 10 minutes DIAD was added dropwise. Ice-bath was removed and the reaction mixture was stirred at room temperature for 48 hours. The product was purified using flash chromatography, using pure ethyl acetate. The product 14a (2.78 g, 7.64 mmol, 84%) was afforded as a yellow oil. H-NMR (CDCl$_3$): δ 7.39 (2H, d, J=8.62), 7.36 (5H, m), 6.91 (2H, d, J=8.58), 5.38 (1H, dd, J=3.11, 3.10 Hz), 3.03 (1H, dd, J=8.39, 8.38), 2.71 (1H, dd, J=3.14, 3.14), 2.63 (4H, b), 2.44 (4H, b), 2.27 (3H, s).

3. General Procedure for Preparation of the Hydrochloride Salts 13b to 16b from Free Amines 13a to 16a: Preparation of Hydrochloride Salt 13b from Free Amine 13a To a solution of 1.0 g of product 13a (3.18 mmol) in 10 mL of stirring THF under N$_2$, 10 equivalents of 2M HCl in andydrous diethyl ether (15.9 mL, 31.8 mmol) was added at room temperature. The mixture was allowed to stir for 12 to 16 hours. The reaction mixture was then filtered and redissolved in 10 mL of anhydrous ethyl alcohol. The reaction was heated to reflux conditions for 5 to 10 minutes, and the solvent was then evaporated by reduced pressure yielding 0.83 g of the final product 13b (2.38 mmol, 75%) as a white-cream solid. The hydrochloride salt product was confirmed by treating a sample of the product with strong base, extracting with diethyl ether, evaporating the organic layer under reduced pressure, and confirming by NMR in CDCl$_3$. The NMR data corresponded with the free amine product 13a.

EXAMPLE 6

[$^3$H] 5-HT UPTAKE ASSAY

A [$^3$H]5-HT uptake assay was performed to determine the ability of the 2-(4-fluorophenoxy)-2-phenyl-ethyl piperazines (Compounds 10b, 11b, and 12b) to inhibit [$^3$EC]5-HT uptake (Dorsey et al., 2004). The specific uptake of [$^3$H]5-HT by human platelets was typically >90% specific as defined by 10 μM fluoxetine.

Outdated human platelets were obtained from the blood bank at Pitt County Memorial Hospital, Greenville, N.C. Platelets from 5-10 donors were pooled, 10% dimethylsulfoxide was added, and aliquots were stored frozen at −80° C. until use. For assays, 5 ml of platelets were thawed and suspended in 20 mL ice-cold Krebs-Ringer-HEPES (KRH) buffer as previously described (Cozzi and Foley, 2002). The KRH buffer contained the following ingredients: 124.0 mM NaCl, 2.9 mM KCl, 1.3 mM MgSO$_4$, 1.2 mM KH$_2$PO$_4$, 2.4 mM CaCl$_2$, 5.2 mM d-glucose, 25.0 mM HEPES, 0.1 mM sodium ascorbate, 0.1 mM pargyline. The buffer was adjusted to pH 7.4 with 5 M NaOH. The ability of platelets to accumulate [$^3$H] serotonin was measured in the absence and presence of test drugs as follows: a 490 μaliquot of the platelet suspension was added to glass tubes containing 5 μl test drug (various concentrations, dissolved in DMSO), 5 μl DMSO (for total determinations), or 5 μl fluoxetine hydrochloride dissolved in DMSO (for nonspecific determinations; final concentration, 10 μM). The assay tubes were preincubated in a 37° C. shaking water bath for 5 min. The tubes were then returned to the ice bath and chilled for 10 min. [$^3$H] Serotonin was added 5 μl of stock solution; final concentration, 10 nM), giving a total incubation volume of 500 μl. All tubes were returned to the 37° C. shaking water bath for 5 min to initiate neurotransmitter uptake. Uptake was terminated by chilling the test tubes in the ice bath. After adding 3 ml ice-cold KRH, each assay tube was immediately vacuum filtered through glass fiber filters (Whatman GF/B) pretreated with 0.1% polyethyleneimine. Filters were washed with 2×3 ml ice-cold KRH, allowed to dry briefly under vacuum, then placed in liquid scintillation vials. Scintillation cocktail (8 ml) was added and the vials were sealed, vortexed, and allowed to stand overnight. Radioactivity was measured using liquid scintillation spectroscopy (Packard Tri-Carb 1600 CA). Specific uptake was defined as uptake at 37° C. minus uptake in the presence of 10 μM fluoxetine. Under these conditions, specific [$^3$H] serotonin uptake was typically 90% of total uptake. The IC$_{50}$ value for each test drug was determined from displacement curves using at least 6 drug concentrations, each run in triplicate. Data were transformed from dpm to % specific uptake and fitted to a four-parameter logistic curve using commercial computer software, from which the IC$_{50}$ values are obtained. The IC50 values are shown in Table 1 below.

TABLE 1

| CMPD %# | IC$_{50}$ (μM) SERT |
| --- | --- |
| 10b | 1.45 |
| 11b | 3.27 |
| 12b | 9.56 |

Figure 9:
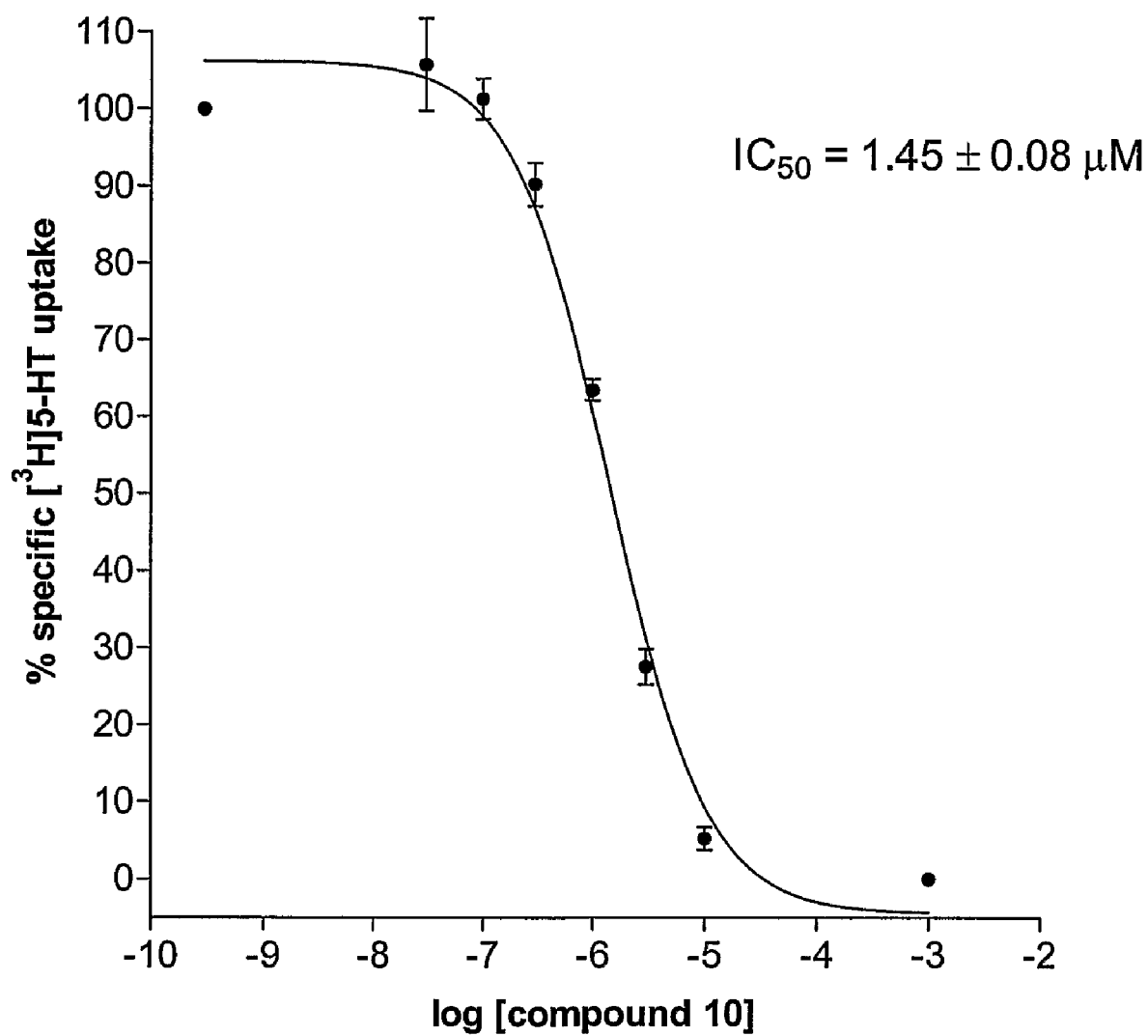
FIG. 9 shows the inhibition of [$^3$H]5-HT uptake into human platelets by Compound 10b.
Figure 10:
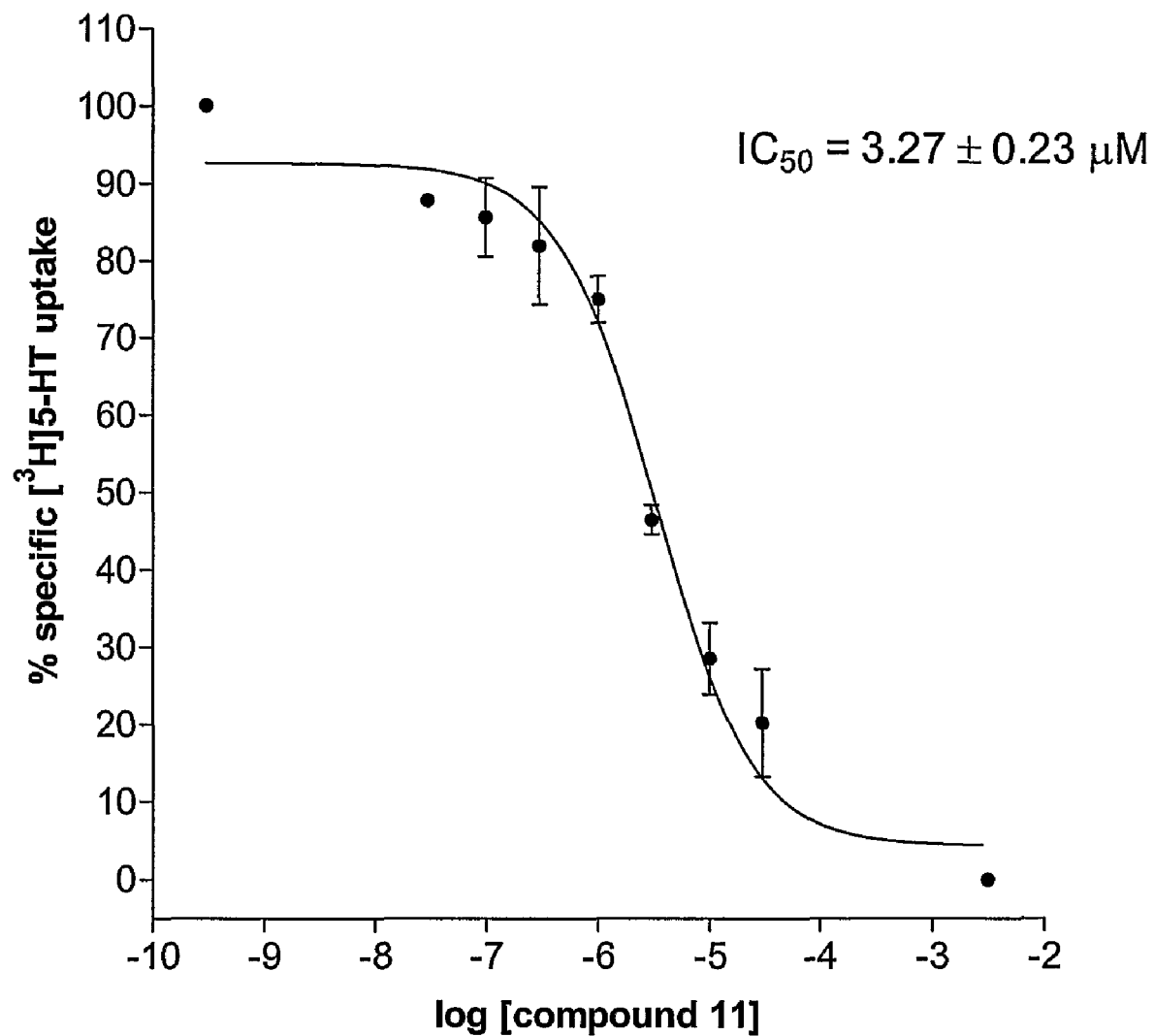
FIG. 10 shows the inhibition of [$^3$H]5-HT uptake into human platelets by Compound 11b.
Figure 11:
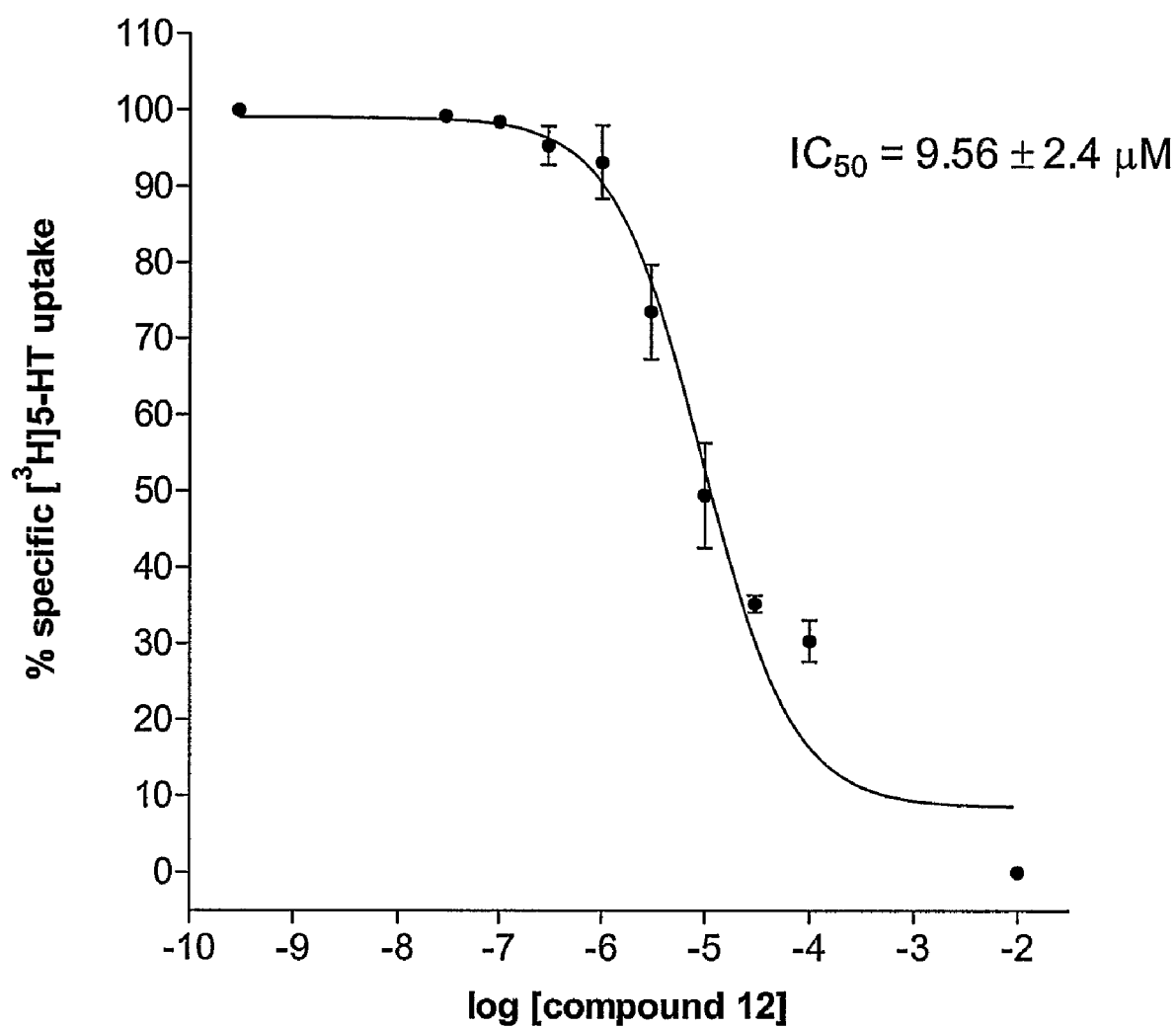
FIG. 11 shows the inhibition of [$^3$H]5-HT uptake into human platelets by Compound 12b.

Dose-response curves for inhibition of [$^3$H]5-HT uptake by Compounds 10b, 11b, and 12b are presented in FIGS. 9-11. The inhibition curves all had slope coefficients that did not differ from unity, indicating that the compounds all interacted with a single site on the serotonin reuptake transporter (SERT). Compounds 10b and 11b were the most potent inhibitors of [$^3$H]5-HT accumulation, with IC$_{50}$ values of 1.45±0.08 μM and 3.27±0.23 μM, respectively. These values did not differ from each other at the P<0.05 level of significance (one-way ANOVA followed by a Student-Newman-Keuls t-test). Compound 12b was the least potent compound in the series with an IC$_{50}$ value of 9.56±2.4 μM; this was only one-sixth the potency of compound 10b and three-fold less potent than compound 1b1 (P<0.05). It is apparent that the new compounds are significantly less potent than fluoxetine, which exhibits nanomolar (nM) affinity for the SERT, but it is not possible at this stage to decide whether the decreased potency is due to electrostatic, stereochemical, or steric considerations or some combination of these. For example, the phenylpiperazine moiety of the new compounds adds considerable bulk to the side-chain amine of fluoxetine and also changes its electronic character with the addition of new lone pair electrons and an electron-rich aromatic ring. Without wanting to be bound by theory, it is possible that the electron-withdrawing, hydrophobic trifluoromethyl group present on the phenyl ring of 12b is responsible for the attenuated serotonin uptake inhibition activity of this compound when compared to compounds 10b and 11b, but the methoxy substitution on compound 11b also represents a positional isomer and this may influence binding through a steric mechanism.

EXAMPLE 7

Biological Evaluation

Biological Evaluation of selected compounds was done through the National Institutes of Health Psychoactive Drug Screening Program (NIH-PDSP). Biological evaluation of the synthesized molecules consisted of: (a) Neurotransmitter uptake assays for the human serotonin transporter (SERT), (b) Binding assays for the serotonin receptor $5\text{-}HT_{1A}$, (c) Binding assays for the serotonin receptor $5\text{-}HT_{2A}$, and (d) Comparison of the biological data obtained for the synthesized molecules with that of currently used psychotherapeutics.

All binding assays were carried out with an incubation time of 60 minutes at room temperature. All binding assays were performed in a similar manner, although the buffers used differ from assay to assay.

a. Binding Assays for the 5-HT Receptor Subtypes

Table 2 below gives the (1) radioligand; (2) assay buffer; (3) unlabelled reference ligand; and (4) references to the commonly-known procedures which were used.

TABLE 2

| Serotonin | Radioligand | Assay buffer | Unlabelled ligand as reference compound | References |
|---|---|---|---|---|
| 5-HT1A | 3H-8-OH-DPAT | A | 5-HT | Roth lab standard protocol |
| 5-HT2A | 3H-ketanserin | A | Chlorpromazine | Roth lab Standard protocol |

The assay buffer A was made up of 50 mM Tris-Cl, 0.1 mM EDTA, and 10 mM $MgCl_2$, at a pH of 7.4. To perform the assay, a 96-well plate was set up as follows:

| | | | | | | | |
|---|---|---|---|---|---|---|---|
| UNK #1 | UNK #1 | UNK #2 | UNK #2 | UNK #3 | UNK #3 | UNK #4 | UNK #4 |
| UNK #5 | UNK #5 | UNK #6 | UNK #6 | UNK #7 | UNK #7 | UNK #8 | UNK #8 |
| UNK #9 | UNK #9 | UNK #10 | UNK #10 | UNK #11 | UNK #11 | UNK #12 | UNK #12 |
| STD #1 | STD #1 | STD #2 | STD #2 | TOTAL BINDING | TOTAL BINDING | TOTAL BINDING | TOTAL BINDING |
| STD #1 | STD #1 | STD #1 | STD #1 | STD #1 | STD #1 | STD #1 | STD #1 |
| AT 1 nM | AT 1 nM | AT 3 nM | AT 3 nM | AT 10 nM | AT 10 nM | AT 30 nM | AT 30 nM |
| STD #1 | STD #1 | STD #1 | STD #1 | STD #1 | STD #1 | TOTAL | TOTAL |
| AT 100 nM | AT 100 nM | AT 300 nM | AT 300 nM | AT 1000 nM | AT 1000 nM | COUNTS ADDED/ PLATE | COUNTS ADDED/ PLATE |

For the 3H-ligands 1-2 nM final concentration of radioligand was used. For 125I-radioligands, 0.05-0.1 nM final concentration was used. The following components were pipetted in the following order: binding buffer, radioligand, cold unknown ligand, cold reference ligand, and membranes. The wells were incubated at room temperature for 60 minutes. At the end of the incubation, the samples were harvested onto pre-soaked (0.3% polyethyleneimine) GF/C filters using a 96-well harvester. They were then washed with 3 quick washes using ice-cold harvest buffer. The filters were removed and air dried overnight. Samples were counted in a 96-well counter using 100 µl of scintillant/well. The Ki value of the reference compound was calculated using the LIGAND Program (Munson and Rodbard, 1980). The percent inhibition was calculated using the following formula:

$$\text{Inhibition} = \text{Counts bound at 10 uM concentration of unknown compound} \times 100 \text{ Total specific counts}$$

b. Binding Assays for the Transporters

Representative Ki values for transporters have already been determined as follows:

5-HTT: Imipramine Ki=12+/−2 nM

VMAT: Ketanserin=20 +/−1 nM

NET: Nisoxetine=1+/0.5 nM

Table 3 below gives the (1) radioligand; (2) assay buffer; and (3) unlabelled reference ligand.

TABLE 3

| Transporter | Radioligand | Assay buffer | Unlabelled ligand as reference compound |
|---|---|---|---|
| SERT | 3H-Citalopram | H | Fluoxetine |

The assay buffer H contained 50 mM Tris-HCl, 150 nM NaCl, and 5 mM KCl, at a pH of 7.4. For the peptide receptor binding assay, filters were pre-soaked for 7 days in 0.3% PEI. To perform the assay, a 96-well plate was set up as follows:

| | | | | | | | |
|---|---|---|---|---|---|---|---|
| UNK #1 | UNK #1 | UNK #2 | UNK #2 | UNK #3 | UNK #3 | UNK #4 | UNK #4 |
| UNK #5 | UNK #5 | UNK #6 | UNK #6 | UNK #7 | UNK #7 | UNK #8 | UNK #8 |
| UNK #9 | UNK #9 | UNK #10 | UNK #10 | UNK #11 | UNK #11 | UNK #12 | UNK #12 |
| STD #1 | STD #1 | STD #2 | STD #2 | TOTAL BINDING | TOTAL BINDING | TOTAL BINDING | TOTAL BINDING |
| STD #1 | STD #1 | STD #1 | STD #1 | STD #1 | STD #1 | STD #1 | STD #1 |
| AT 1 nM | AT 1 nM | AT 3 nM | AT 3 nM | AT 10 nM | AT 10 nM | AT 30 nM | AT 30 nM |
| STD #1 | STD #1 | STD #1 | STD #1 | STD #1 | STD #1 | TOTAL COUNTS ADDED/ PLATE | TOTAL COUNTS ADDED/ PLATE |
| AT 100 nM | AT 100 nM | AT 300 nM | AT 300 nM | AT 1000 nM | AT 1000 nM | | |

For the 3H-ligands 1-2 nM final concentration of radioligand was used. For 125I-radioligands, 0.05-0.1 nM final concentration was used. The following components were pipetted in the following order: binding buffer, radioligand, cold unknown ligand, cold reference ligand, and membranes. The wells were incubated at room temperature for 60 minutes. At the end of the incubation, the samples were harvested onto pre-soaked (0.3% polyethyleneimine) GF/C filters using a 96-well harvester. They were then washed with 3 quick washes using ice-cold harvest buffer. The filters were removed and air dried overnight. Samples were counted in a 96-well counter using 100 μl of scintillant/well. The Ki value of the reference compound was calculated using the LIGAND Program (Munson and Rodbard, 1980). The percent inhibition was calculated using the following formula:

Inhibition=Counts bound at 10 μM concentration of unknown compound×100 Total Specific Counts In Table 4 below, data represent mean % inhibition (N=4 determinations) for compounds tested at receptor subtypes. In Table 53 below, Data represent Ki Values. Ki values are reported in nanomolar concentration. Significant inhibition is considered >50%. If the result was <50%, NIH-PDSP did not provide the information.

TABLE 4

| CMPD # | 5-HT1A | 5-HT2A | SERT |
|---|---|---|---|
| 1b | 100.0 | 96.0 | 62.0 |
| 2b | 91.0 | 81.0 | 67.0 |
| 3b | 98.0 | 61.0 | 12.0 |
| 4b | 93.0 | 7.0 | 16.0 |
| 5b | 71.0 | 17.0 | 22.0 |
| 6b | 102.0 | 11.0 | −1.0 |
| 7b | 76.0 | −2.0 | 16.0 |

TABLE 5

| | Ki (nM) | | |
|---|---|---|---|
| CMPD # | 5-HT1A | 5-HT2A | SERT |
| 1b | 102.0 | 237.1 | 1,242.00 |
| 2b | 716.1 | 195.2 | 1,871.00 |
| 3b | 257.9 | 3,493.0 | — |
| 4b | 375.3 | — | — |
| 5b | 712.5 | — | — |
| 6b | 88.7 | — | — |
| 7b | 724.4 | — | — |
| 8-OH-DPAT | 1.2[a] | >1000[a] | >1000[a] |
| mirtazapine | >1000[a] | 14.8[a] | >1000[a] |
| fluoxetine | >1000[a] | >1000[a] | 30.8[a] |

[a]Orjales, et al. 2003.

Ten (10) of the sixteen (16) compounds synthesized were biologically evaluated. Compounds 10b, 11b and 12b were previously evaluated for their serotonin uptake ability as described in Example 5. For screening purposes, compounds 1b through 7b were analyzed for their affinity towards the serotonin 5-HT$_{1A}$ receptor as well as their affinity towards the 5-HT$_{2A}$ receptor and the SERT. Data in Table 2 represent mean % inhibition (N=4 determinations) for compound tested at receptor subtypes. Significant inhibition is considered >50%. In cases where negative inhibition (−) is seen, this represents a stimulation of binding. Occasionally, compounds at high concentrations will non-specifically increase binding. Ki values were determined only for compounds with % inhibition >50%. As can be seen in Table 3, all the compounds show low to moderate affinity for $^{5}$-HT$_{1A}$. Compound 6b shows the highest affinity for 5-HT$_{1A}$. Compounds 1b and 2b exhibit the desired dual activity towards the 5-HT$_{2A}$ receptor and the SERT, although low. None of the compounds has exhibited significant affinity for SERT; however, compounds 1b and 2b show low affinity which is still higher than that showed by compounds 10b through 12b (see Table 1 in Example 5).

REFERENCES CITED

The entire content of each of the references given below is hereby incorporated by reference.

Blier, P.; de Montigny, C.; Chaput, Y. *J. Clin. Psychiatry* 1990, vol. 51, 4 (suppl.), 14-20.

Cozzi, N. V.; Foley, K. F. *Biotechniques.* 2002, vol. 32, 486.

Dorsey, J. M., Miranda, M. G., Cozzi, N. V., Pinney, K. G. *Bioorganic & Medicinal Chem.* 2003, vol. 12, 1483-91.

Gonzalez-Heydrich, J.; Peroutka, S. J. *J. Clin. Psychiatry* 1990, vol. 51, 4 (suppl.), 5-12.

Hyttel, J. *Prog. Neuro-Psychopharmacol & Biol. Psychiat.* 1982, vol. 6, 281.

Lemberger, L.; Fuller, R. W.; Zerbe, R. L. *Clinical Neuropharmacology* 1985, vol. 8, 4, 299-317.

Modell, J. G.; Katholi, C. R.; Modell, J. A.; DePalma, R. L. *Clinical Pharmacology and Therapeutics* 1997, vol. 61, 4, 476-487.

Munson, P. J., and Rodbard, D. *Anal. Biochem.* 1980, vol. 107, 220-239

Orjales, et al. *J. Med. Chem.* 2003, vol. 46(25); 5512-5532.

What is claimed is:
1. A compound having the general formula:
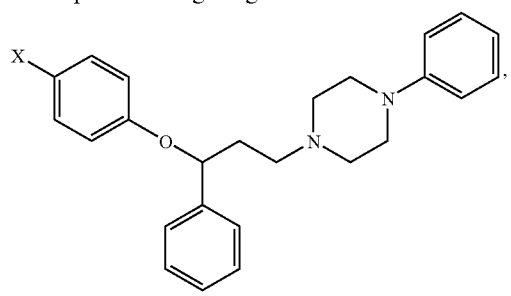
wherein X is F; and
salt thereof.
2. A compound having the general formula:
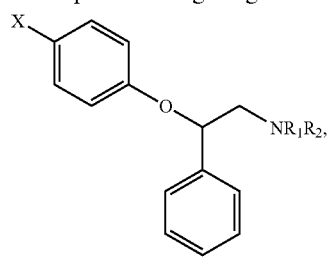
wherein X is F;
wherein $NR_1R_2$ is:
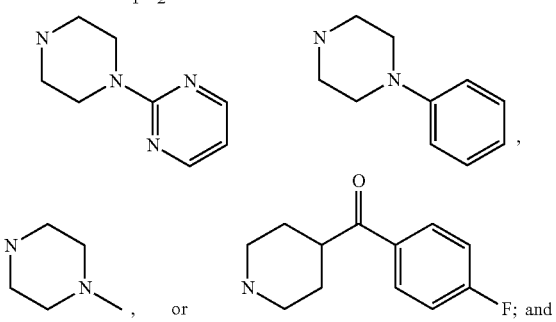
F; and
salt thereof.
3. A compound having the formula:
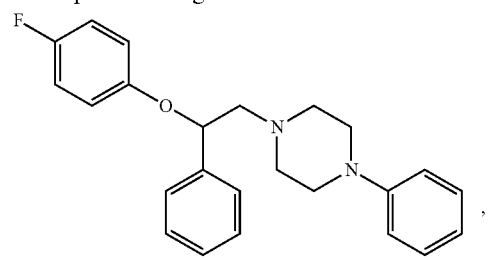
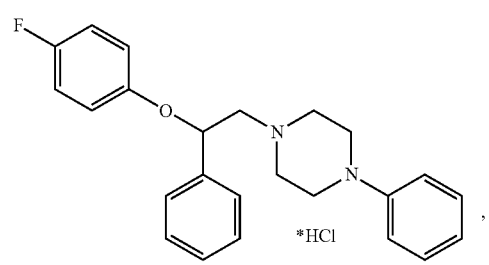
-continued
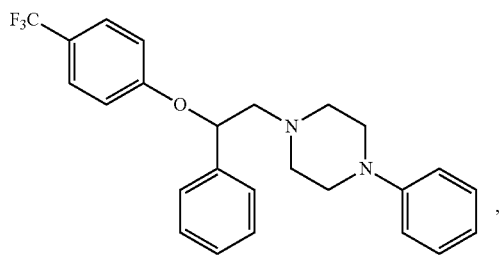
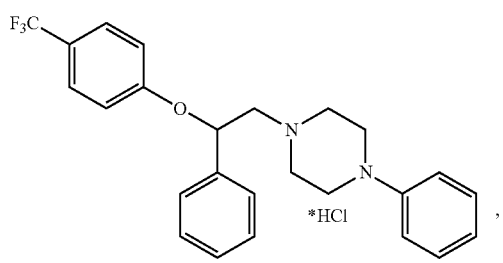
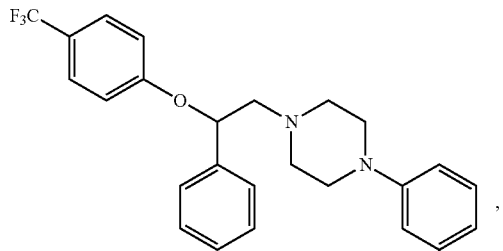
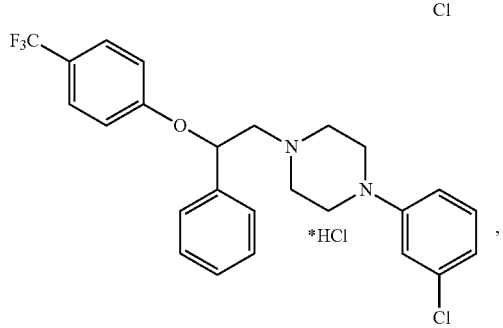
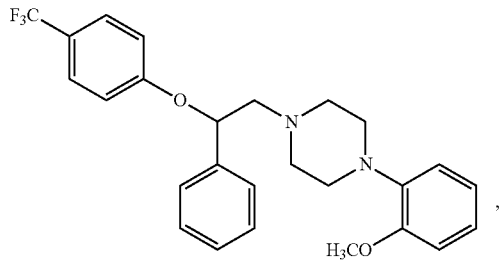
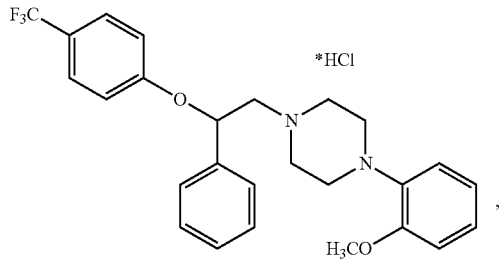

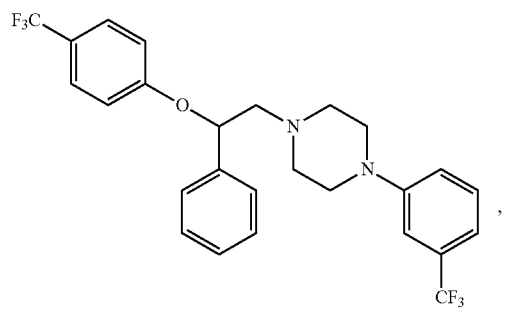,
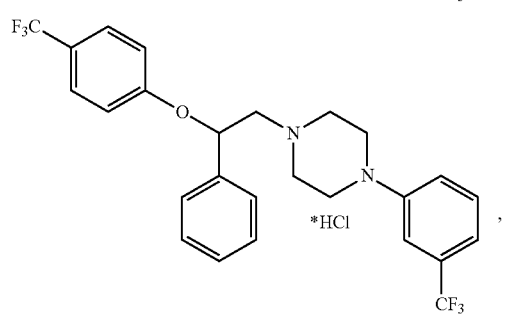,
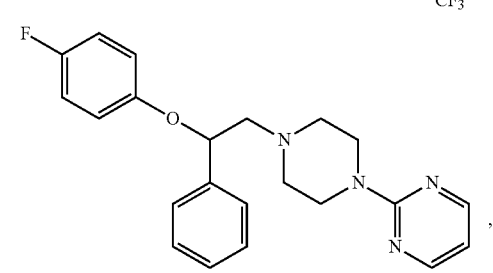,
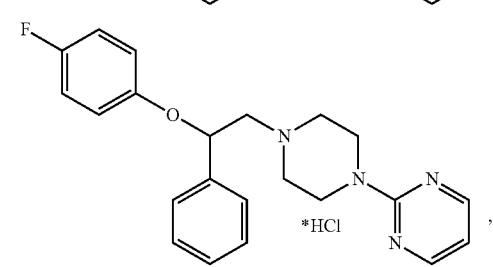,
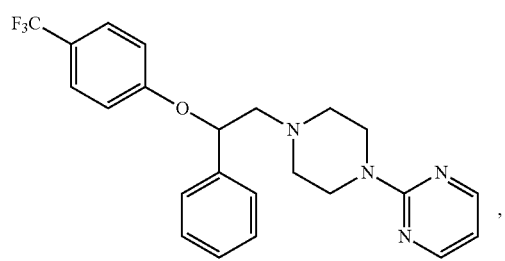,
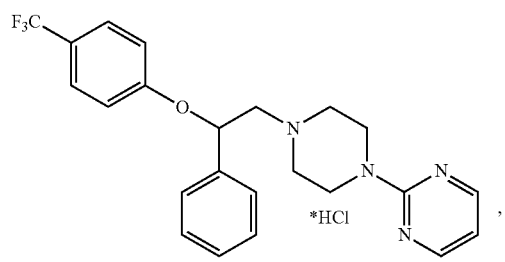,
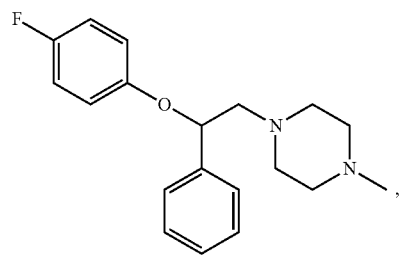,
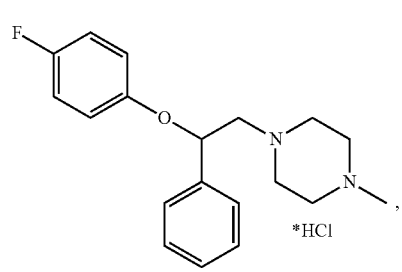,
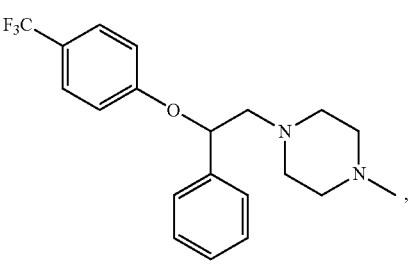,
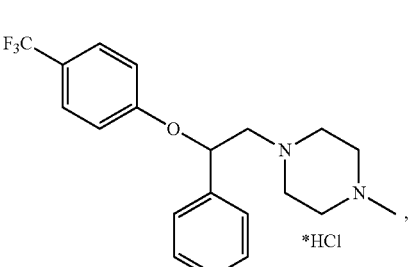,
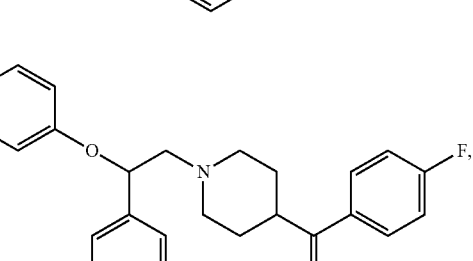,
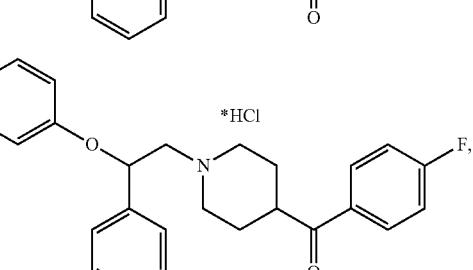, -continued
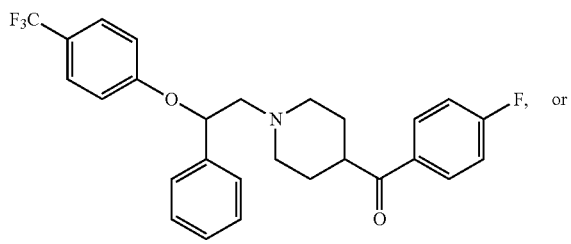
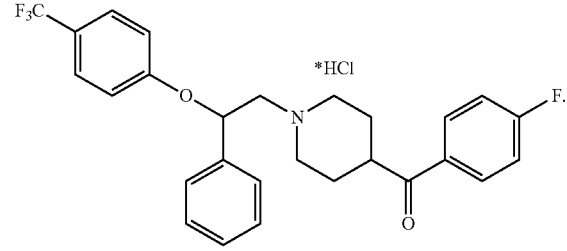
* * * * *